(12) United States Patent
Zitzmann et al.

(10) Patent No.: US 7,816,560 B1
(45) Date of Patent: Oct. 19, 2010

(54) LONG CHAIN N-ALKYL COMPOUNDS AND OXA-DERIVATIVES THEREOF

(75) Inventors: Nicole Zitzmann, Oxford (GB); Terry D. Butters, Oxfordshire (GB); Frances M. Platt, Oxfordshire (GB); Gary S. Jacob, Creve Coeur, MO (US); Donald H. Picker, Warren, NJ (US); Sandra Carrouee, Lyons (FR); George W. J. Fleet, Oxfordshire (GB); Raymond A. Dwek, Oxfordshire (GB); David Durantel, Arles (FR); Anand Mehta, Langdale, PA (US); Timothy M. Block, Doylestown, PA (US)

(73) Assignees: Thomas Jefferson University, Philadelphia, PA (US); The Chancellor, Masters and Scholars of the University of Oxford, Oxford (GB); United Therapeutics Corporation, Silver Spring, MD (US)

( * ) Notice: Subject to any disclaimer, the term of this patent is extended or adjusted under 35 U.S.C. 154(b) by 1464 days.

(21) Appl. No.: 10/031,145

(22) PCT Filed: Aug. 10, 2000

(86) PCT No.: PCT/US00/21732
§ 371 (c)(1),
(2), (4) Date: Jul. 3, 2002

(87) PCT Pub. No.: WO01/10429
PCT Pub. Date: Feb. 15, 2001

Related U.S. Application Data

(60) Provisional application No. 60/148,101, filed on Aug. 10, 1999, provisional application No. 60/198,621, filed on Apr. 20, 2000.

(51) Int. Cl.
C07C 211/00 (2006.01)
C07C 303/00 (2006.01)
C07C 307/00 (2006.01)
C07C 309/00 (2006.01)

(52) U.S. Cl. .............................. 564/1; 564/23
(58) Field of Classification Search ................. 514/315, 514/352, 351, 353, 354
See application file for complete search history.

(56) References Cited

U.S. PATENT DOCUMENTS 4,246,345 A 1/1981 Kinast et al.

(Continued)

FOREIGN PATENT DOCUMENTS

EP 0 367 747 A 5/1990

(Continued)

OTHER PUBLICATIONS

Mellor et al. "High-Performance Cation-Exchange Chromatrography and Pulsed Amperometric Detection for the Separation, Detection and Quantitation of N-Alkylated Imino Sugars in Biological Samples" Aug. 2000, Analytical Biochemistry, 284(1), 136-42.*

(Continued)

*Primary Examiner*—San-ming Hui
*Assistant Examiner*—Kathrien Cruz
(74) *Attorney, Agent, or Firm*—Foley & Lardner LLP

(57) ABSTRACT

Long chain N-alkyl amino and imino compounds, oxa-substituted derivatives thereof, and pharmaceutical compositions including such compounds are described. The long chain N-alkyl group is a $C_8$-$C_{16}$ alkyl group. The long chain N-alkyl compounds and oxa-substituted derivatives thereof can be used in the treatment of viral infections, in particular hepatitis B virus or hepatitis C virus, in a cell or an individual. For example, the long chain N-alkyl compounds or oxa-substituted derivatives thereof can be derived from piperidines, pyrrolidines, phenylamines, pyridines, pyrroles, or amino acids.

4 Claims, 8 Drawing Sheets

U.S. PATENT DOCUMENTS

| | | | |
|---|---|---|---|
| 4,266,025 | A | 5/1981 | Kinast et al. |
| 4,405,714 | A | 9/1983 | Kinast et al. |
| 4,806,650 | A | 2/1989 | Schröder et al. |
| 4,861,892 | A | 8/1989 | Fleet |
| 4,894,388 | A | 1/1990 | Fleet |
| 4,910,310 | A | 3/1990 | Campbell et al. |
| 4,944,572 | A | 7/1990 | Young |
| 4,996,329 | A | 2/1991 | Fleet et al. |
| 5,011,929 | A | 4/1991 | Fleet et al. |
| 5,013,842 | A | 5/1991 | Fleet et al. |
| 5,017,704 | A | 5/1991 | Fleet et al. |
| 5,043,273 | A | 8/1991 | Scudder et al. |
| 5,100,797 | A | 3/1992 | Fleet et al. |
| 5,103,008 | A | 4/1992 | Scudder et al. |
| 5,200,523 | A | 4/1993 | Fleet |
| 5,264,356 | A | 11/1993 | Rohrschneider |
| 5,286,877 | A | 2/1994 | Behling et al. |
| 5,310,745 | A | 5/1994 | Partis et al. |
| 5,401,645 | A | 3/1995 | Grabner et al. |
| 5,580,884 | A * | 12/1996 | Platt et al. .......... 514/315 |
| 5,596,005 | A | 1/1997 | Wong et al. |
| 5,622,972 | A | 4/1997 | Bryant et al. |
| 5,643,888 | A | 7/1997 | Rohrschneider |
| 6,291,657 | B1 | 9/2001 | Platt et al. |
| 6,355,413 | B1 | 3/2002 | Gage et al. |
| 6,462,197 | B2 * | 10/2002 | Hollingsworth et al. ..... 546/243 |
| 6,465,487 | B1 | 10/2002 | Block et al. |
| 6,465,488 | B1 | 10/2002 | Butters et al. |
| 6,545,021 | B1 | 4/2003 | Mueller et al. |
| 6,660,749 | B2 | 12/2003 | Butters et al. |
| 6,689,759 | B1 | 2/2004 | Jacob et al. |
| 6,809,083 | B1 | 10/2004 | Mueller et al. |
| 7,256,005 | B2 * | 8/2007 | Zitzmann et al. ............. 435/7.2 |
| 2006/0094671 | A1 | 5/2006 | Jacob et al. |
| 2006/0106065 | A1 | 5/2006 | Jacob et al. |
| 2006/0252918 | A1 | 11/2006 | Rowlands et al. |
| 2006/0264468 | A1 | 11/2006 | Mueller et al. |

FOREIGN PATENT DOCUMENTS

| | | |
|---|---|---|
| EP | 0 445 098 A2 | 2/1991 |
| WO | WO 92/00277 * | 1/1992 |
| WO | WO 98/35685 A1 | 8/1998 |
| WO | WO 99/24401 * | 5/1999 |
| WO | WO 99/24401 A1 | 5/1999 |
| WO | WO 99/40916 A1 | 8/1999 |
| WO | WO 00/47198 A2 | 8/2000 |
| WO | WO 01/60366 A1 | 8/2001 |
| WO | WO 2004/005333 A1 | 1/2004 |

OTHER PUBLICATIONS van den Broek et al. (Synthesis of oxygen-substituted N-alkyl 1-deoxynojirimycin derivatives: aza sugar a-glucosidase inhibitors showing antiviral (HIV-1) and immunosuppressive activity, Recl. Trav. Chim. Pays-bas, 1994, vol. 113, pp. 507-5166).*

Defoin et al. (6-Deoxy-Nojirimycin and 6-Deoxy-gulo-Nojirimycin in the racemic and D-series, D-Fuco-Nojirimycin and their 1-Deoxyderivatives via Hetero-Diels-Alder Cycloadditions, 1997, Tetrahedron, vol. 53, No. 40, pp. 13783-13796).*

Acosta et al., "Agents for treating human immunodeficiency virus infection," Am. J. Hosp. Pharm., Sep. 15, 1994, 51:2251-2267.

Berge et al., "Pharmaceutical Salts," J. Pharm. Sci., Jan. 1977, 66(1):1-19.

Bergeron et al., "Calnexin: a membrane-bound chaperone of the endoplasmic reticulum," TIBS Mar. 19, 1994, Elsevier Scient Ltd. 0968-0004/94 pp. 124-128.

Block et al., "Secretion of human hepatitis B virus is inhibited by the imino sugar N-butyldeoxynojirimycin," PNAS, Mar. 1994, 91:2235-2239.

Blum et al., "Antiviral therapy of hepatitis B virus infection: Blocking viral gene expression," Advanced Drug Delivery Reviews, 1995, 17:321-331.

Branza-Nichita et al., "Antiviral of N-Butyledeoxynojirimycin against Bovine Viral Diarrhea Virus Coorelates with Misfolding of E2 Envelope Proteins and Impairment of Their Association into E1-E2 Heterodimers," (2001) J. Virol. 75(8), pp. 3527-3536.

Bruss et al., The role of envelope proteins in hepatitis B virus assembly, PNAS, Feb. 1991, 88:1059-1063.

Carrère-Kremer et al., "Subcellular Localization and Topology of the p7 Polypeptide of Hepatitis C Virus," Journal of Virology, Apr. 2002, 76(8):3720-3730.

Choukhi et al., Involvement of Endoplasmic Reticulum Chaperones in the Folding of Hepatitus C Virus Glycoproteins, (1998) J. Virol., 72(5), pp. 3851-3858.

Coates et al., "Developments in viral hepatitis during 1994," Exp. Opin. Ther. Patents, 1995, 5(8):747-756.

Courageot et al., "a-Glucosidase Inhibitors Reduce Dengue Virus Production by Affecting the Initial Steps of Virion Morphogenesis in the Endoplasmic Reticulum," (2000) J. Virol., 74(1): pp. 564-572.

De Francesco et al., "Biochemical and immunologic properties of the nonstructural proteins of the hepatitis C virus: implications for development of antiviral agents and vaccines," Semin. Liver Dis., 2000, 20(1):69-83, one page Abstract only.

Di Bisceglie, Adrian M., "Hepatitis C and Hepatocellular Carcinoma," Hepatology, Sep. 1997, 26(3)Suppl. 1:345-350.

Doong et al., "Inhibition of the replication of hepatitis B virus in vitro by 2',3'-dideoxy-3'-thiacytidine and related analogues," PNAS, Oct. 1991, 88:8495-8499.

Duff et al., "The Transmembrane Domain of Influenza A M2 Protein Forms Amantadine-Sensitive Proton Channels in Planar Lipid Bilayers," Virology 190, pp. 485-489 (1992) 0042-6822/92 Copyright 1992 by Academic Press, Inc.

Durantel et al., "Study of the Mechanism of Antiviral Action of Iminosugar Derivatives against Bovine Viral Diarrhea Virus," (2001) J. Virol. 75(19): pp. 8987-8998.

Dwek, et al., "Targeting Glycosylation as a Therapeutic Approach," Nature Reviews/Drug Discovery, vol. 1, Jan. 2002, pp. 65-75. Glycobiology Institute, Dept. of Biochemistry, University of Oxford, Oxford OX1 3QU, UK.

Elbein et al., "Inhibitors of the biosynthesis and processing of N-linked oligosaccharide chains," Ann. Rev. Biochem., 1987, 56:497-534.

Esposito et al., "Synthesis of amphiphilic polyhydroxylated pyrrolidones as potential glycosidase inhibitors," Tetrahedron Lett., 1998, 39(36):6543-6546.

Fischer et al., "Amantadine blocks channel activity of the transmembrane segment of the NB protein from influenza B," Eur. Biophys J. (2001) 30: pp. 416-420, DOI 10.1007/s00240100157.

Fleet et al., "Enantiospecific synthesis of deoxymannojirimycin, fagomine and 2R,5R-dihydroxymethyl-3R,4R-dihydroxypyrrolidine from D-glucose," Tetrahedron Letters, 1985, 26(11):1469-1472.

Fourel et al., "The Carbocyclic Analog of 2'-Deoxyguanosine Induces a Prolonged Inhibition of Duck Hepatitis B Virus DNA Synthesis in Primary Hepatocyte Cultures and in the Liver," J. Virol., Feb. 1994, 68(2):1059-1065.

Gabrielson et al., "Synthesis and Antiviral Evaluation of N-Carboxamidine-Substituted Analogues of 1-β-D-Ribofuranosyl-1,2,4-triazole-3-carboxamidine Hydrochloride," J. Med. Chem., 1992, 35:3231-3238.

Ganem, D., "Assembly of *Hepadnaviral virions* and Subviral Particles," Curr. Top. Microbiol. Immunol., 1991, 168:61-83.

Griffin et al., "A conserved basic loop in hepatitis C virus p7 protein is required for amantidine-sensitive ion channel activity in mammalian cells but is dispensable for localization to mitochondria," Journal of General Virology, 2004, 85:451-461.

Griffin et al., "The p7 protein of hepatitis C virus forms an ion channel that is blocked by the antiviral drug, Amantadine," FEBS Letters 535 (2003) pp. 34-38, Elsevier Science B.V. on behalf of the Federation of European Biochemical Societies.

Guidotti et al., "Interleukin-2 and Alpha/Beta Interferon Down-Regulate Hepatitis B Virus Gene Expression in Vivo by Tumor Necrosis Factor-Dependent and -Independent Pathways," J. Virol., Mar. 1994, 68(3):1265-1270.

Harada et al., "E2-p7 Region of the Bovine Viral Diarrhea Virus Polyprotein: Processing and Functional Studies," (2000) J. Virol. 74(20): pp. 9498-9506.

Hay et al., "The molecular basis of the specific anti-influenza action of amantadine," EMBO Journal, vol. 4 No. 11 pp. 3021-3024, 1985. 'Oxford, England.

Henzler et al., "Avoiding viral contamination in biotechnological and pharmaceutical processes," Nature Biotechnology, Nov. 1998, 16:1077-1078.

Hoofnagle et al., "The Treatment of Chronic Viral Hepatitis," New Engl. J. Med., Jan. 30, 1997, 336(5):347-356.

Lin et al., "Processing in the Hepatitis C Virus E2-NS2 Region: Identification of p7 and Two Distinct E2-Specific Products with Different C Termini," (1994) J. Virol. 68(8): pp. 5063-5073.

Locarnini et al., "Hepatitis B: New approaches for antiviral chemotherapy," Antiviral Chemistry & Chemotherapy, 1996, 7(2):53-64.

Lohmann et al., "Replication of Subgenomic Hepatitis C Virus RNAs in a Hepatoma Cell Line," (1999) Science, 285(5424) pp. 110-113.

Lu et al., "Aberrant trafficking of hepatitis B virus glycoproteins in cells in which N-glycan processing is inhibited," PNAS, Mar. 1997, 94:2380-2385.

Martin et al., "Pilot Study of Recombinant Human Granulocyte-macrophage Colony-stimulating Factor in the Treatment of Chronic Hepatitis B," Hepatology, Oct. 1993, 18(4):778-780.

Mehta et al., "a-Glucosidase inhibitors as potential broad based antiviral agents," FEBS Left. Jun. 23, 1998; 430(1-2); pp. 17-22.

Mehta et al., "Hepatitis B virus (HBV) envelope glycoproteins vary drastically in their sensitive to glycan processing: Evidence that alteration of a single N-linked glycosylation site can regulate HBV secretion," PNAS, Mar. 1997, 94:1822-1827.

Miller et al., "Heptatitis C virus shares amino acid sequence similarity with pestiviruses and flaviviruses as well as members of two plant virus supergroups," PNAS, Mar. 1990, 87:2057-2061.

Mizushima et al., "Two Hepatitis C Virus Glycoprotecin E2 Products with Different C Termini," (1994) J. Virol. 68(10); pp. 6215-6222.

Montal et al., "Formation of Bimolecular Membranes from Lipid Monolayers and a Study of Their Electrical Properties," Proc. Nat. Acad. Sci. USA 69 (1972) pp. 3561-3566.

Pavlovic et al., "The hepatitis C virus p7 protein forms an ion channel that is inhibited by long-alkyl-chain iminosugar derivatives," PNAS May 13, 2003; 100(10): pp. 6104-6108.

Peterson et al., "Transient, Lectin-like Association of Calreticulin with Folding Intermediates of Cellular and Viral Glycoproteins," Molecular Biology of the Cell, vol. 6, pp. 1173-1184, Sep. 1995 by The American Society for Cell Biology.

Pietschmann et al., "Characterization of Cell Lines Carrying Self-Replicating Hepatitis C Virus RNAs," (2001) J. Virol. 75(3); pp. 1252-1264.

Reed et al., "Overview of Hepatitis C Virus Genome Structure, Polyprotein Processing, and Protein Properties," Department of Molecular Microbiology, Washington University School of Medicine, St. Louis, MO, pp. 55-84, 2000.

Rokitskaya et al., "Effect of Avidin on Channel Kinetics of Biotinylated Gramicidin," Biochemistry, 2000, 39:13053-13058.

Sakai et al., "The p7 polypeptide of hepatitis C virus is critical for infectivity and contains functionally important genotype-specific sequences," PNAS, Sep. 30, 2003, 100(20):11646-11651.

Saunier et al., "Inhibition of N-linked Complex Oligosaccharide Formation by 1-Deoxynojirimycin, and Inhibitor of Processing Glucosidases," J. Biol. Chem., Dec. 1982, 257(23):14155-14161.

Smith JP, "Treatment of chronic hepatitis C with amantadine," Dig. Dis. Sci., Aug. 1997, 42(8):1681-1687, one page Abstract only.

Sullivan et al., "A nested polymerase chain reaction assay to differentiate pestiviruses," Virus Res., 1995, 38:231-239.

Sunstrom, et al., "Ion Channels Formed by NB, an Influenza B Virus Protein," J. Membrane Biol. 150, pp. 127-132 (1996).

Swartz et al., "An Inhibitor of the Kv2.1 Potassium Channel Isolated from the Venom of a Chilean Tarantula," Neuron, Oct. 1996, 15:941-948.

Van Den Broek et al., "Chemical modification of azasugars, inhibitors of N-glycoprotein-processing glycosidases and of HIV-1 infection," Recl. Trav. Chim. Pays-Bas, 1993, 112:82-94.

Wu et al., "Antiviral Effects of an Iminosugar Derivative on Flavivirus Infections," (2002) J. Virol., 76(8): pp. 3596-3604.

Xu et al., "Synthesis of a novel hepatitis C virus protein by ribosomal frameshift," (2001) The EMBO Journal 20(14): pp. 3840-3848.

Zitzmann, et al., "Imino sugars inhibit the formation and secretion of bovine viral diarrhea virus, a pestivirus model of hepatitis C virus: Implications for the development of broad spectrum anti-hepatitis virus agents," PNAS, Oct. 12, 1991, 96(21):11878-11882.

* cited by examiner

N-Nonyl-DGJ

N-nonyl-MeDGJ

N-nonyl-altrostatin

N-nonyl-2-aminobenzamide (2ABC9)

N-nonyl-DHDP nonylamine

LONG CHAIN N-ALKYL COMPOUNDS AND OXA-DERIVATIVES THEREOF

This application is the National Stage Entry of International Application PCT/US00/21732, filed 10 Aug. 2000, which International Application designated the U.S., which International Application was published under PCT article 21(2) in English and which International Application claims Priority from U.S. Provisional Application No. 60/198,621, filed Apr. 20, 2000, and from U.S. Provisional Application No. 60/148,101, filed Aug. 10, 1999.

FIELD OF THE INVENTION

This invention relates to long chain N-alkyl amino and imino compounds and oxa-derivatives thereof for treating pestivirus and flavivirus infections of animals and humans.

BACKGROUND OF THE INVENTION

HCV is an RNA virus belonging to the Flaviviridae family. Individual isolates consist of closely related, yet heterologous populations of viral genomes. This genetic diversity enables the virus to escape the host's immune system, leading to a high rate of chronic infection. The flavivirus group to which HCV belongs is known to include the causative agents of numerous human diseases transmitted by arthropod vectors. Human diseases caused by flaviviruses include various hemorrhagic fevers, hepatitis, and encephalitis. Viruses known to cause these diseases in humans have been identified and include, for example, yellow fever virus, dengue viruses 1-4, Japanese encephalitis virus, Murray Valley encephalitis virus, Rocio virus, West Nile fever virus, St. Louis encephalitis virus, tick-borne encephalitis virus, Louping ill virus, Powassan virus, Omsk hemorrhagic fever virus, and Kyasanur forest disease virus. A critical need therefore also exists for treating animals, as well as humans, infected with at least one virus, such as a flavivirus and/or pestivirus.

More than 40 million people worldwide are chronically infected with the hepatitis C virus (HCV), and this represents one of the most serious threats to the public health of developed nations (Hoofnagle et al., *New Engl. J. Med.* 336:347-356, 1997). Hepatitis C infection is the cause of more than 10,000 deaths annually in the United States (*Washington Post*, Nov. 11, 1997, at A2), a number that is expected to triple in the next twenty years in the absence of effective intervention. Chronic HCV also increases the risk of liver cancer. There are more than 40 million people worldwide who are chronically infected with HCV, representing one of the most serious threats to the public health of developed nations (Hoofnagle et al., ibid.). Persistent infection develops in as many as 85% of HCV patients and in at least 20% of these patients the chronic infection leads to cirrhosis within twenty years of onset of infection. With an estimated 3.9 million North Americans chronically infected, complications from hepatitis C infection are now the leading reasons for liver transplantation in the United States.

Another causative agent of acute and chronic liver disease including liver fibrosis, cirrhosis, inflammatory liver disease, and hepatic cancer is hepatitis B virus (HBV) (Joklik, *Virology*, 3$^{rd}$ Ed., Appleton & Lange, Norwalk, Conn., 1988). Although effective vaccines are available, there are still more than 300 million people worldwide, i.e., 5% of the world's population, chronically infected with the virus (Locamini et al., *Antiviral Chemistry & Chemotherapy* 7:53-64, 1996). Such vaccines have no therapeutic value for those already infected with the virus. In Europe and North America, between 0.1% to 1% of the population is infected. Estimates are that 15% to 20% of individuals who acquire the infection develop cirrhosis or another chronic disability from HBV infection. Once liver cirrhosis is established, morbidity and mortality are substantial, with about a 5-year patient survival period (Blume et al., *Advanced Drug Delivery Reviews* 17:321-331, 1995). It is therefore necessary and of high priority to find improved and effective anti-HBV anti-hepatitis therapies (Locamini et al., ibid.).

Therapeutic interventions which are effective for treatment of HCV infection are limited in number and effectiveness. Standard treatment for HCV infection includes administration of interferon-alpha. However, interferon-alpha is of limited use in about 20% of the HCV-infected population (Hoofnagle et al., ibid.) and treatment with this compound results in long-term improvement in only 5% of patients. Furthermore, the complications and limitations of interferon-alpha seriously limit the applicability of the treatment. An experimental treatment comprising administration of interferon-alpha and ribavirin (1-β-D-ribofuranosyl-1H-1,2,4-triazole-3-carboxamide) resulted in long-term improvement in only half of the patients suffering a relapse of HCV infection (*Washington Post*, Nov. 11, 1997, at A2). Clearly, the disappointing results with interferon must prompt a search for more effective and less toxic therapeutics. Thus, a critical need remains for a therapeutic intervention that effectively treats HCV infection or supplements those otherwise available.

In addition to those people chronically infected with HCV, there are more than 350 million people chronically infected with hepatitis B virus (HBV). More than 150 million of these people are likely to die from liver disease in the absence of intervention. As many as 20 million HBV carriers reside in developed nations, as do most HCV carriers. A large number of individuals who are infected with HCV are also infected with HBV. The therapy for combined HBV/HCV infection is particularly challenging because the HBV and HCV viruses differ from one another in therapeutically significant ways. HBV is a hepadnavirus, while HCV is a pestivirus. HBV is a DNA-containing virus, the genome of which is replicated in the nucleus of the infected cell using a combination of a DNA-dependent RNA polymerase and an RNA-dependent DNA polymerase (i.e., a reverse transcriptase). HCV is an RNA-containing virus, the genome of which is replicated in the cytoplasm of the infected cell using one or more types of RNA-dependent RNA polymerases. Despite the frequent concurrence of HBV infection and HCV infection, a number of compounds known to be effective for treating HBV infection are not effective against HCV. For example, lamivudine (the nucleoside analog 3TC) is useful for treating HBV infection, but is not useful for treating HCV infection. The difference in the susceptibility of HBV and HCV to antiviral agents no doubt relates to their genetically based replicative differences. There remains a particularly critical need for a therapeutic intervention that effectively treats both HBV and HCV infection.

Other hepatitis viruses significant as agents of human disease include hepatitis A, hepatitis Delta, hepatitis E, hepatitis F, and hepatitis G (Coates et al., *Exp. Opin. Ther. Patents* 5:747-756, 1995). In addition, there are animal hepatitis viruses that are species specific. These include, for example, those infecting ducks, woodchucks, and mice. The availability of animal models allows the preclinical testing of antiviral compounds for each class of virus. Furthermore, animal viruses can cause significant losses to the livestock industry (Sullivan et al., *Virus Res.* 38:231-239, 1995). Such animal viruses include pestiviruses and flaviviruses such as bovine viral diarrhea virus (BVDV), classical swine fever virus, border disease virus, and hog cholera virus.

SUMMARY OF THE INVENTION

In general, the invention features long chain N-alkyl amino and imino compounds and oxa-substituted derivatives thereof and includes pharmaceutical compositions containing an effective amount of such compounds. The long chain N-alkyl group is a $C_8$-$C_{16}$ alkyl group. The long chain N-alkyl compounds and oxa-substituted derivatives thereof can be used in the treatment of viral infections in a cell or an individual. In an individual, the infection may result in chronic or acute disease and treatment of same may reduce the severity of infection (e.g., production of virus) or disease symptoms. The long chain N-alkyl compounds may or may not inhibit glycosidase activity or glycoplipid synthesis at a detectable level; preferred are compounds that do not inhibit α-glucosidase activity at a detectable level but still are effective in treating infection. For example, the long chain N-alkyl compounds and oxa-substituted derivatives can be derived from a piperidine, a pyrrolidine, a phenylamine, a pyridine, a pyrrole, or an amino acid.

In one aspect, the invention features a nitrogen-containing virus-inhibiting compound including an N-$C_8$-$C_{16}$ alkyl group. Preferably, the compound includes an N-$C_8$-$C_{10}$ alkyl group (e.g., N-nonyl or N-decyl group) or an N-$C_8$-$C_{10}$ oxa-alkyl group such as an N-$(CH_2)_6O(CH_2)_nCH_3$ group or N-$(CH_2)_2O(CH_2)_{n+4}CH_3$ group for n=1, 2 or 3. The nitrogen-containing virus-inhibiting compound can have an inhibitory concentration ($IC_{50}$) of about 20 μM or less, preferably about 10 μM or less, and more preferably about 5 μM or less, for the inhibition of one or more pestiviruses or a flaviviruses in an assay (e.g., plaque formation, yield). In particular, a compound effective against both a pestivirus and a flavivirus (e.g., HBV and BVDV) is preferred.

In another aspect, the invention features a method of inhibiting morphogenesis of a virus. The method includes administering an effective amount of the nitrogen-containing virus-inhibiting compound, or a pharmaceutically acceptable salt thereof, to a cell or an individual infected with the virus. The cell can be a mammalian cell or a human cell.

In yet another aspect, the invention features a method of treating an individual infected with a virus. The method includes administering an effective amount of the nitrogen-containing virus-inhibiting compound, or a pharmaceutically acceptable salt thereof, to an individual infected with a virus. The treatment can reduce, abate, or diminish the virus infection in the animal or human. The animal can be a bird or mammal (e.g., pig, cow, mice). The nitrogen-containing virus-inhibiting compound can be administered orally.

In another aspect, the invention features a method of manufacturing a pharmaceutical composition comprising combining at least one nitrogen-containing virus-inhibiting compound including an N-$C_8$-$C_{16}$ alkyl group or an oxa-substituted derivative thereof with a pharmaceutically acceptable carrier.

The compound can have the formula:

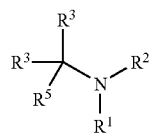

in which $R^1$ is a $C_8$-$C_{16}$ alkyl; and can also contain 1 to 5, preferably 1 to 3, and more preferably 1 to 2 oxygen atoms (i.e., oxa-substituted derivatives). Preferred oxa-substituted derivatives are 3-oxanonyl, 3-oxadecyl, 7-oxanonyl and 7-oxadecyl.

$R^2$ is hydrogen, $R^3$ is carboxy, or a $C_1$-$C_4$ alkoxycarbonyl, or $R^2$ and $R^3$, together are

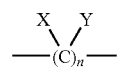

or —$(CXY)_n$—, wherein n is 3 or 4, each X, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, or an aroyloxy, and each Y, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, an aroyloxy, or deleted (i.e., not present);

$R^4$ is hydrogen or deleted (i.e., not present); and $R^5$ is hydrogen, hydroxy, amino, a substituted amino, carboxy, an alkoxycarbonyl, an aminocarbonyl, an alkyl, an aryl, an aralkyl, an alkoxy, a hydroxyalkyl, an acyloxy, or an aroyloxy, or $R^3$ and $R^5$, together, form a phenyl and $R^4$ is deleted (i.e., not present). When $R^2$ and $R^3$, together, are —$(CXY)_n$— and $R^4$ is deleted (i.e., not present), all Y are deleted (i.e., not present). The compound can be a physiologically acceptable salt or solvate of the compound.

In certain embodiments, $R^1$ is a $C_8$-$C_{10}$ alkyl (e.g., $C_9$ alkyl) and $R^2$ can be hydrogen, $R^3$ can be carboxy, or a $C_1$-$C_4$ alkoxycarbonyl, $R^4$ can be hydrogen, and $R^5$ can be hydrogen, hydroxy, amino, a substituted amino, carboxy, an alkoxycarbonyl, an aminocarbonyl, an alkyl, an aryl, an aralkyl, an alkoxy, a hydroxyalkyl, an acyloxy, or an aroyloxy. In certain preferred embodiments, $R^3$ is carboxy. In other preferred embodiments, $R^3$ and $R^5$, together, form a phenyl and $R^4$ is deleted (i.e., not present). In yet other preferred embodiments, $R^2$ and $R^3$, together, are —$(CXY)_n$—.

In certain embodiments, the compound has the formula:

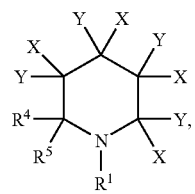 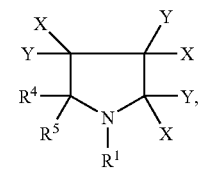

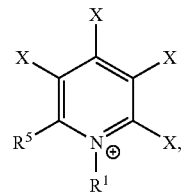 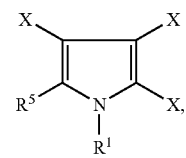

-continued

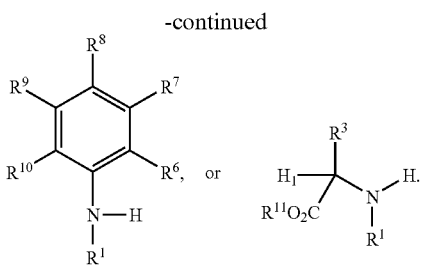

Each of $R^6$-$R^{10}$, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, or an aroyloxy, and $R^{11}$ is hydrogen, or a $C_1$-$C_4$ alkyl.

The nitrogen-containing virus inhibiting compound can be N-alkylated piperidines, N-oxa-alkylated piperidines, N-alkylated pyrrolidines, N-oxa-alkylated pyrrolidines, N-alkylated phenylamines, N-oxa-alkylated phenylamines, N-alkylated pyridines, N-oxa-alkylated pyridines, N-alkylated pyrroles, N-oxa-alkylated pyrroles, N-alkylated amino acids, or N-oxa-alkylated amino acids. In certain embodiments, the N-alkylated piperidine, N-oxa-alkylated piperidine, N-alkylated pyrrolidine, or N-oxa-alkylated pyrrolidine compound can be an imino sugar. For example, preferred nitrogen-containing virus-inhibiting compounds are N-nonyl-1,5-dideoxy-1,5-imino-D-galactitol (N-nonyl-deoxygalactonojirimycin or N-nonyl DGJ), N-(7-oxa-nonyl)-1,5-dideoxy-1,5-imino-D-galactitol (N-7-oxa-nonyl DGJ), N-nonyl-1,5,6-trideoxy-1,5-imino-D-galactitol (N-nonyl MeDGJ), N-(7-oxa-nony)-1,5,6-trideoxy-1,5-imino-D-galactitol (N-7-oxa-nonyl MeDGJ), N-nonyl altrostatin, N-nonyl-2R,5R-dihydroxymethyl-3R,4R-dihydroxypyrrolidine (N-nonyl DMDP), N-nonyl-deoxynojirimycin (N-nonyl DNJ), N-nonyl-2-aminobenzamide (2ABC9), or a derivative, an enantiomer or a stereoisomer thereof. The structures of unsubstituted compounds are shown in FIG. 1.

In certain embodiments, the virus can be a flavivirus or a pestivirus. Infections by flaviviruses include, but are not limited to, those caused by a yellow fever virus, a dengue virus (e.g., dengue viruses 1-4), a Japanese encephalitis virus, a Murray Valley encephalitis virus, a Rocio virus, a West Nile fever virus, a St. Louis encephalitis virus, a tick-borne encephalitis virus, a Louping ill virus, a Powassan virus, an Omsk hemorrhagic fever virus, and a Kyasanur forest disease virus. Infections by pestiviruses include, but are not limited to, those caused by hepatitis C virus (HCV), rubella virus, a bovine viral diarrhea virus (BVDV), a classical swine fever virus, a border disease virus, or a hog cholera virus.

According to yet another aspect, the invention features a prophylactic method for protecting a mammal infected by a virus from developing hepatitis or a heptacellular cancer that is among the sequelae of infection by the virus, including administering to the virus infected cell of the animal an effective anti-viral amount of the nitrogen-containing virus-inhibiting compound.

DESCRIPTION OF THE INVENTION

Figure 1:
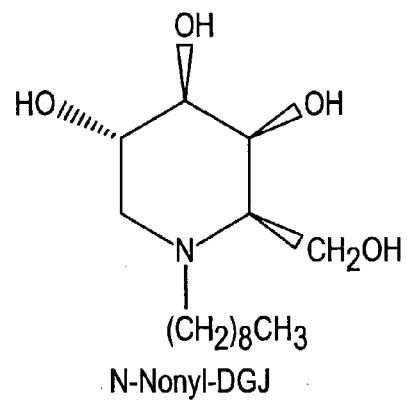
FIG. 1 depicts chemical structures for compounds which were used in this study.
Figure 1:
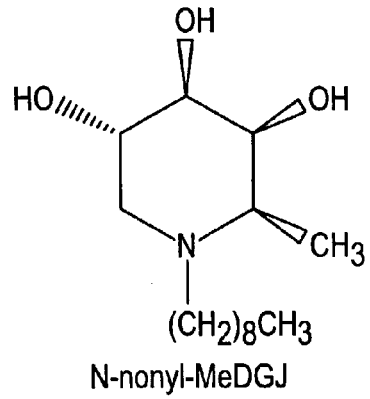
Figure 1:
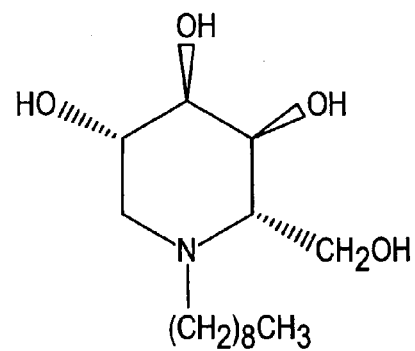
Figure 1:
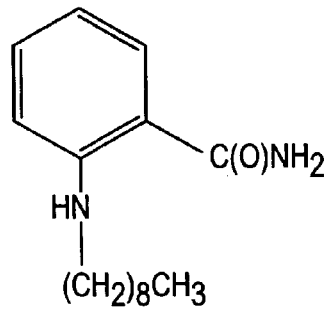
Figure 1:
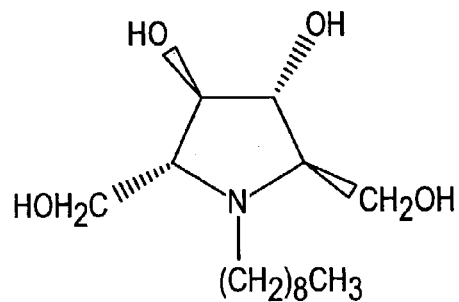
Figure 1:
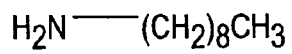

The nitrogen-containing virus-inhibiting compound includes an N-$C_8$-$C_{16}$ alkyl group, such as an N-$C_8$-$C_{10}$ alkyl group, particularly a nonyl or decyl group, or an oxa-substituted derivative thereof. The nitrogen-containing virus-inhibiting compound can be an N-alkylated piperidine, N-oxa-alkylated piperidine, N-alkylated pyrrolidine, N-oxa-alkylated pyrrolidine, N-alkylated phenylamine, N-oxa-alkylated phenylamine, N-alkylated pyridine, N-oxa-alkylated pyridine, N-alkylated pyrrole, N-oxa-alkylated pyrrole, N-alkylated amino acid, or N-oxa-alkylated amino acid such as N-nonyl DGJ, N-oxa-nonyl DGJ, N-nonyl MeDGJ, N-oxa-nonyl MeDGJ, N-nonyl altrostatin, N-nonyl DMDP, N-oxa-nonyl DMDP, N-nonyl-2-aminobenzamide, or N-oxa-nonyl-2-aminobenzamide.

The compound can have the formula:

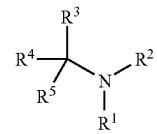

in which $R^1$ is a $C_8$-$C_{16}$ alkyl, $R^2$ is hydrogen, $R^3$ is carboxy, or a $C_1$-$C_4$ alkoxycarbonyl, $R^4$ is hydrogen, and $R^5$ is hydrogen, hydroxy, amino, a substituted amino, carboxy, an alkoxycarbonyl, an aminocarbonyl, an alkyl, an aryl, an aralkyl, an alkoxy, a hydroxyalkyl, an acyloxy, or an aroyloxy. Alternatively, $R^1$ is a $C_8$-$C_{16}$ alkyl, $R^2$ is hydrogen, $R^3$ and $R^5$, together, form a phenyl, which can be substituted or unsubstituted, and $R^4$ is deleted (i.e., not present). In another alternative, $R^1$ is a $C_8$-$C_{16}$ alkyl, $R^4$ is hydrogen or deleted (i.e., not present), $R^5$ is hydrogen, hydroxy, amino, a substituted amino, carboxy, an alkoxycarbonyl, an aminocarbonyl, an alkyl, an aryl, an aralkyl, an alkoxy, a hydroxyalkyl, an acyloxy, or an aroyloxy, and $R^2$ and $R^3$, together, are

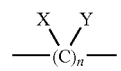

or —$(CXY)_n$—, wherein n is 3 or 4, each X, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, or an aroyloxy, and each Y, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, an aroyloxy, or deleted. When $R^2$ and $R^3$, together, are —(CXY)$_n$— and $R^4$ is deleted, all Y are deleted. The compound can be a physiologically acceptable salt or solvate of the compound.

In certain embodiments, the compound has the formula:

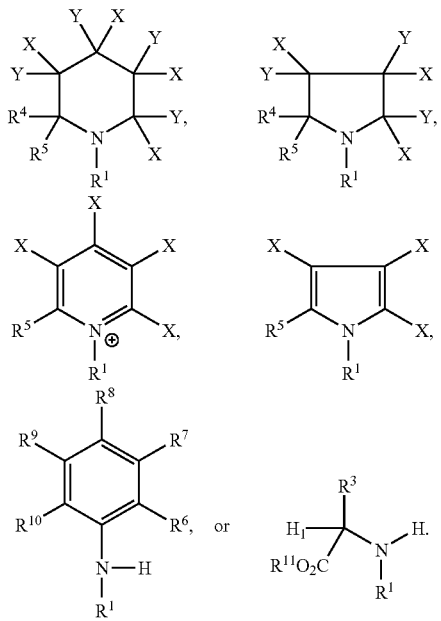

Each of $R^6$-$R^{10}$, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, or an aroyloxy, and $R^{11}$ is hydrogen, or a $C_1$-$C_4$ alkyl.

As used herein, the groups have the following characteristics, unless the number of carbon atoms is specified otherwise. Alkyl groups have from 1 to 16 carbon atoms and are linear or branched, substituted or unsubstituted. Alkoxy groups have from 1 to 16 carbon atoms, and are linear or branched, substituted or unsubstituted. Alkoxycarbonyl groups are ester groups having from 2 to 16 carbon atoms. Alkenyloxy groups have from 2 to 16 carbon atoms, from 1 to 6 double bonds, and are linear or branched, substituted or unsubstituted. Alkynyloxy groups have from 2 to 16 carbon atoms, from 1 to 3 triple bonds, and are linear or branched, substituted or unsubstituted. Aryl groups have from 6 to 14 carbon atoms (e.g., phenyl groups) and are substituted or unsubstituted. Aralkyloxy (e.g., benzyloxy) and aroyloxy (e.g., benzoyloxy) groups have from 7 to 15 carbon atoms and are substituted or unsubstituted. Amino groups can be primary, secondary, tertiary, or quaternary amino groups (i.e., substituted amino groups). Aminocarbonyl groups are amido groups (e.g., substituted amido groups) having from 1 to 32 carbon atoms. Substituted groups can include a substituent selected from the group consisting of halogen, hydroxy, $C_{1-10}$ alkyl, $C_{2-10}$ alkenyl, $C_{1-10}$ acyl, or $C_{1-10}$ alkoxy.

The N-alkylated amino acid can be an N-alkylated naturally occurring amino acid, such as an N-alkylated α-amino acid. A naturally occurring amino acid is one of the 20 common α-amino acids (Gly, Ala, Val, Leu, Ile, Ser, Thr, Asp, Asn, Lys, Glu, Gln, Arg, His, Phe, Cys, Trp, Tyr, Met, and Pro), and other amino acids that are natural products, such as norleucine, ethylglycine, ornithine, methylbutenyl-methylthreonine, and phenylglycine. Examples of amino acid side chains (e.g., $R^5$) include H (glycine), methyl (alanine), —$CH_2C(O)NH_2$ (asparagine), —$CH_2$—SH (cysteine), and —$CH(OH)CH_3$ (threonine).

A long chain N-alkylated compound can be prepared by reductive alkylation of an amino (or imino) compound. For example, the amino or imino compound can be exposed to a long chain aldehyde, along with a reducing agent (e.g., sodium cyanoborohydride) to N-alkylate the amine. Similarly, a long chain N-oxa-alkylated compound can be prepared by reductive alkylation of an amino (or imino) compound. For example, the amino or imino compound can be exposed to a long chain oxa-aldehyde, along with a reducing agent (e.g., sodium cyanoborohydride) to N-oxa-alkylate the amine.

The compounds can include protecting groups. Various protecting groups are well known. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the invention. Further examples and conditions are found in Greene, *Protective Groups in Organic Chemistry*, (1$^{st}$ Ed., 1981, Greene & Wuts, 2$^{nd}$ Ed., 1991).

The compounds can be purified, for example, by crystallization or chromatographic methods. The compound can be prepared stereospecifically using a stereospecific amino or imino compound as a starting material.

The amino and imino compounds used as starting materials in the preparation of the long chain N-alkylated compounds are commercially available (Sigma, St. Louis, Mo.; Cambridge Research Biochemicals, Norwich, Cheshire, United Kingdom; Toronto Research Chemicals, Ontario, Canada) or can be prepared by known synthetic methods. For example, the compounds can be long chain N-alkylated imino sugar compounds or oxa-substituted derivatives thereof. The imino sugar can be, for example, deoxygalactonojirmycin (DGJ), 1-methyl-deoxygalactonojirimycin (MeDGJ), deoxynorjirimycin (DNJ), altrostatin, 2R,5R-dihydroxymethyl-3R,4R-dihydroxypyrrolidine (DMDP), or derivatives, enantiomers, or stereoisomers thereof.

The syntheses of a variety of imino sugar compounds have been described. For example, methods of synthesizing DNJ derivatives are known and are described, for example, in U.S. Pat. Nos. 5,622,972, 5,200,523, 5,043,273, 4,994,572, 4,246,345, 4,266,025, 4,405,714, and 4,806,650, and U.S. patent application Ser. No. 07/851,818, filed Mar. 16, 1992. Methods of synthesizing other imino sugar derivatives are known and are described, for example, in U.S. Pat. Nos. 4,861,892, 4,894,388, 4,910,310, 4,996,329, 5,011,929, 5,013,842, 5,017,704, 5,580,884, 5,286,877, and 5,100,797. The enantiospecific synthesis of 2R,5R-dihydroxymethyl-3R,4R-dihydroxypyrrolidine (DMDP) is described by Fleet & Smith (*Tetrahedron Lett.* 26:1469-1472, 1985).

The substituents on the imino sugar compound can influence the potency of the compound as an antiviral agent and additionally can preferentially target the molecule to one organ rather than another. Methods for comparing the potencies of various substituted compounds are provided in the Examples.

With the exception of the pyridinium compounds, which are in salt form, the compounds described herein may be used in the free amine form or in a pharmaceutically acceptable salt form. The counter anion of the pyridinium compound can be chloride, tartrate, phosphate, or sulfate. Pharmaceutical salts and methods for preparing salt forms are provided by Berge et al. (*J. Pharm. Sci.* 66:1-18, 1977). Pharmaceutically acceptable salts can be preferred for compounds that are difficult to solubilize in the pharmaceutical composition (e.g., compounds having longer alkyl chains). A salt form is illustrated, for example, by the HCl salt of an amino derivative. The compounds may also be used in the form of prodrugs, such as the 6-phosphorylated DNJ derivatives described in U.S. Pat. Nos. 5,043,273 and 5,103,008. Use of compositions which further comprise a pharmaceutically acceptable carrier and compositions which further comprise components useful for delivering the composition to an animal are explicitly contemplated. Numerous pharmaceutically acceptable carriers useful for delivering the compositions to a human and components useful for delivering the composition to other animals such as cattle are known in the art. Addition of such carriers and components to the composition of the invention is well within the level of ordinary skill in the art. For example, the compounds can be di- or tetra- acetates, propionates, butyrates, or isobutyrates. The compound can be a solvate.

The invention also encompasses isotopically-labeled counterparts of compounds disclosed herein. An isotopically-labeled compound of the invention has one or more atoms replaced with an isotope having a detectable particle- or x-ray-emitting (radioactive) nucleus or a magnetogyric nucleus. Examples of such nuclei include $^2$H, $^3$H, $^{13}$C, $^{15}$N, $^{19}$F, $^{29}$Si, $^{31}$P, $^{32}$P and $^{125}$I. Isotopically-labeled compounds of the invention are particularly useful as probes or research tools for spectrometric analyses, radioimmunoassays, binding assays based on scintillation, fluorography, autoradiography, and kinetic studies such as inhibition studies or determination of primary and secondary isotope effects.

The nitrogen-containing virus-inhibiting compound can be administered to a cell or an individual affected by a virus. The compound can inhibit morphogenesis of the virus, or it can treat the individual. The treatment can reduce, abate, or diminish the virus infection in the animal. For example, the N-nonyl, N-decyl, N-3-oxa-nonyl, N-3-oxa-decyl, N-7-oxa-nonyl, and N-7-oxa-decyl compounds are antiviral. The antiviral activity is substantially unrelated to the remaining functionalities of the compound.

The nitrogen-containing virus-inhibiting compound combined with at least one other antiviral compound, such as an inhibitor of a viral DNA or RNA polymerase and/or protease, and/or at least one inhibitor of expression of viral genes, replication of the viral genome, and/or assembly of a viral particle. The supplemental antiviral compound may be any antiviral agent, which is presently recognized, or any antiviral agent which becomes recognized. By way of example, the supplemental antiviral compound may be interferon-alpha, interferon-beta, ribavirin, lamivudine, brefeldin A, monensin, TUVIRUMAB™ (Protein Design Labs) PENCICLOVIR™ (SmithKline Beecham), FAMCICLOVIR™ (SmithKline Beecham), BETASERON™ (Chiron), THERADIGM-HBV™ (Cytel), Adefovir Dipivoxil (GS 840, Gilead Sciences); INTRON A™ (Schering Plough), ROFERON™ (Roche Labs), BMS 200,475 (Bristol Myers Squibb), LOBUCAVIR™ (Bristol Myers Squibb), FTC (Triangle Pharmaceuticals), DAPD (Triangle Pharmaceuticals), thymosin alpha peptide, Glycovir (Block et al., *Proc. Natl. Acad. Sci. USA* 91:2235-2240, 1994), granulocyte macrophage colony stimulating factor (Martin et al., *Hepatology* 18:775-780, 1993), an "immune-cytokine" (Guidotti et al., *J. Virol.* 68:1265-1270, 1994), CDG (Fourel et al., *J. Virol.* 68:1059-1065, 1994), or the like.

Long chain N-alkyl compounds are agents that exhibit an inhibitory effect on viral expression. While certain short chain N-alkyl derivatives of imino sugars (e.g., N-butyl DNJ) are potent inhibitors of the N-linked oligosaccharide processing enzymes, such as α-glucosidase I and α-glucosidase II (Saunier et al., *J. Biol. Chem.* 257:14155-14161, 1982; Elbein, *Ann. Rev. Biochem.* 56:497-534, 1987). Some long chain N-alkyl compounds of the invention may exhibit substantially little or no inhibition of a glycosidase enzyme, especially in comparison with N-butyl DNJ or N-nonyl DNJ. Unexpectedly, some long chain N-alkyl compounds do effectively inhibit viral morphogenesis in cells infected with a virus, such as a flavivirus or pestivirus. For example, the nitrogen-containing virus-inhibiting compound can have an $IC_{50}$ of about 10 μM or less, preferably about 3 μM or less, for the inhibition of BVDV or another virus, but the same compounds may exhibit little activity against glycosidases or inhibition of glycolipid synthesis.

Methods for treating a mammal infected with respiratory syncytial virus (RSV) using DNJ derivatives have been described in U.S. Pat. No. 5,622,972. The use of DNJ and N-methyl-DNJ has also been disclosed to interrupt the replication of non-defective retroviruses such as human immunodeficiency virus (HIV), feline leukemia virus, equine infectious anemia virus, and lentiviruses of sheep and goats (U.S. Pat. Nos. 5,643,888 and 5,264,356; Acosta et al., *Am. J. Hosp. Pharm.* 51:2251-2267, 1994).

In the absence of a suitable cell culture system able to support replication of human HCV, bovine viral diarrhea virus (BVDV) serves as the FDA approved model organism for HCV, as both share a significant degree of local protein region homology (Miller & Purcell, *Proc. Natl. Acad. Sci. USA* 87:2057-2061, 1990), common replication strategies, and probably the same subcellular location for viral envelopment. Compounds found to have an antiviral effect against BVDV are highly recommended as potential candidates for treatment of HCV.

The cytotoxicity resulting from exposure of mammalian cells in tissue culture to bovine viral diarrhea virus (BVDV) is prevented by addition of a nitrogen-containing virus-inhibiting compound to the tissue culture medium. The virus inhibitors that were used in the examples below included long chain N-alkyl derivatives of DGJ. Because BVDV is an accepted tissue culture model of HCV (Henzler & Kaiser, *Nature Biotechnology* 16:1077-1078, 1998), the compositions and methods described herein for inhibiting morphogenesis of BVDV are also useful for inhibiting morphogenesis of HCV.

The amount of antiviral agent administered to an animal or to an animal cell according to the methods of the invention is an amount effective to inhibit the viral morphogenesis from the cell. The term "inhibit" as used herein refers to the detectable reduction and/or elimination of a biological activity exhibited in the absence of a nitrogen-containing virus-inhibiting compound according to the invention. The term "effective amount" refers to that amount of composition necessary to achieve the indicated effect. The term "treatment" as used herein refers to reducing or alleviating symptoms in a subject, preventing symptoms from worsening or progressing, inhibition or elimination of the causative agent, or prevention of the infection or disorder in a subject who is free therefrom.

Thus, for example, treatment of viral infection includes destruction of the infecting agent, inhibition of or interference with its growth or maturation, neutralization of its pathological effects, and the like. The amount of the composition which is administered to the cell or animal is preferably an amount that does not induce any toxic effects which outweigh the advantages which accompany its administration.

Actual dosage levels of active ingredients in the pharmaceutical compositions of this invention may be varied so as to administer an amount of the active compound(s) that is effective to achieve the desired therapeutic response for a particular patient.

The selected dose level will depend on the activity of the selected compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient will depend on a variety of factors, including the body weight, general health, diet, time and route of administration and combination with other drugs and the severity of the disease being treated. It is expected that the adult human daily dosage will normally range from between about one microgram to about one gram, preferably from between about 10 mg and 100 mg, of the nitrogen-containing virus-inhibiting compound per kilogram body weight. Of course, the amount of the composition which should be administered to a cell or animal is dependent upon numerous factors well understood by one of skill in the art, such as the molecular weight of the nitrogen-containing virus-inhibiting compound, the route of administration, and the like.

Pharmaceutical compositions that are useful in the methods of the invention may be administered systemically in oral solid formulations, ophthalmic, suppository, aerosol, topical or other similar formulations. For example, it may be in the physical form of a powder, tablet, capsule, lozenge, gel, solution, suspension, syrup, or the like. In addition to the nitrogen-containing virus-inhibiting compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the compound according to the method of the invention. Such pharmaceutical compositions may be administered by any known route. The term "parenteral" used herein includes subcutaneous, intravenous, intraarterial, intrathecal, and injection and infusion techniques, without limitation. By way of example, the pharmaceutical compositions may be administered orally, topically, parenterally, systemically, or by a pulmonary route.

These compositions may be administered according to the methods of the invention in a single dose or in multiple doses which are administered at different times. Because the inhibitory effect of the composition upon a virus may persist, the dosing regimen may be adjusted such that virus propagation is retarded while the host cell is minimally effected. By way of example, an animal may be administered a dose of the composition of the invention once per week, whereby virus propagation is retarded for the entire week, while host cell functions are inhibited only for a short period once per week.

The following specific examples are to be construed as merely illustrative, and not limitive, of the remainder of the disclosure.

EXAMPLES

Preparation of N-nonyl-DGJ (NN-DGJ), N-nonyl-methylDGJ (NN-MeDGJ), N-nonyl-altrostatin, N-nonyl-DNJ (NN-DNJ), N-nonyl-DMDP (NN-DMDP), and N-nonyl-2-aminobenzamide The parent amino or imino compound (DGJ, MeDGJ, altrostatin, DNJ, DMDP, or 2-aminobenzamide (2ABC9) was reductively alkylated with nonylaldehyde (1.2 mol equivalents) in the presence of one mole equivalent of sodium cyanoborohydride for three hours at room temperature in acidified methanol. Typical yields from this reaction were greater than 95% as determined by amperometric detection after high performance cation-exchange chromatography (Dionex). N-Nonyl-compounds were purified from the reaction mixture by high performance liquid chromatography (HPLC) as follows. A sample was applied to a SCX cation-exchange column (7.5×50 mm) in 20% (v/v) acetonitrile and eluted with a linear gradient of 20% acetonitrile containing 500 mM ammonium formate, pH 4.4. The N-nonyl compound was recovered and applied to a C18 reverse-phase column (4.6×250 mm) equilibrated with 10% acetonitrile containing 0.1% trifluoroacetic acid (TFA). The compound was eluted from the column using a linear gradient of 80% acetonitrile containing 0.1% trifluoroacetic acid, lyophilized to dryness, and dissolved in methanol. Samples of purified compound were analyzed by matrix-assisted laser desorption ionization time-of-flight (MALDI-TOF) mass spectrometry using 2,5-dihydroxybenzoic acid as the matrix.

Compounds having different N-alkyl chain lengths are prepared by replacing nonyl aldehyde with the desired chain length aldehyde. Tritiated compounds are prepared by employing tritiated sodium cyanoborohydride as the reducing agent in the reaction.

(a) N-nonyl-DGJ: MALDI-TOF mass spectrometry showed a peak at 288.83 atomic mass units as expected for the structure shown in FIG. 1.

(b) N-nonyl-MeDGJ: MALDI-TOF mass spectrometry showed a peak at 273.9 atomic mass units as expected for the structure shown in FIG. 1.

(c) N-nonyl-altrostatin: MALDI-TOF mass spectrometry showed a peak at 289.44 atomic mass units as expected for the structure shown in FIG. 1.

(d) N-nonyl-DMDP: MALDI-TOF mass spectrometry showed a peak at 287.66 atomic mass units as expected for the structure shown in FIG. 1.

(e) N-nonyl-2-aminobenzamide (2ABC9): MALDI-TOF mass spectrometry showed a peak at 261.57 atomic mass units as expected for the structure shown in FIG. 1.

Preparation of N-(7-oxa-nonyl)-1,5,6-trideoxy-1,5-imino-D-galactitol

Step 1: Synthesis of 2,3;5,6-Di-O-isopropylidene-D-gulono-1,4-lactone

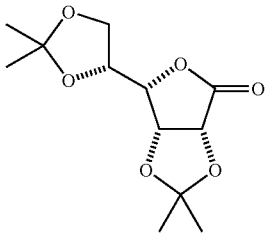

p-Toluenesulfonic acid-monohydrate (1 g) was added to a stirred solution of D-gulono-lactone (20 g, 0.11 mol) in 2,2-dimethoxypropane (60 mL) and dry acetone (200 mL). After 24 hr t.l.c. (ethyl acetate) showed the consumption of starting material ($R_f$ 0.0) and the formation of a major product ($R_f$ 0.8). The reaction mixture was neutralized by stirring with excess sodium hydrogen carbonate, filtered and the solvent removed under reduced pressure. The residue was crystallized from ethyl acetate/hexane to give 2,3;5,6-Di-O-isopropylidene-D-gulono-1,4-lactone as white crystals (26.3 g, 0.1 mol, 91% yield).

M.p. 150-153° C.; $[\alpha]_D^{22}$ +76.2 (c, 0.88 in acetone); $\delta_H$ (200 MHz, CDCl$_3$): 1.28 (s, 6H, C(CH$_3$)$_2$), 1.33, 1.37 (2×s, 6H, C(CH$_3$)$_2$), 3.90 (dd, 1H, J 6.0 Hz, J 9.0 Hz), 4.02-4.10 (m, 1H), 4.18-4.27 (m, 1H), 4.49 (dd, 1H, J$_{3,4}$ 3 Hz, J$_{4,5}$ 9 Hz, H-4), 4.92 (dd, 1H, J$_{2,3}$ 6 Hz, J$_{3,4}$ 3 Hz, H-3), 4.96 (d, 1H, J$_{2,3}$ 6 Hz, H-2); $\delta_C$ (50 MHz, CDCl$_3$): 25.6 (C(CH$_3$)$_2$), 26.3 (C(CH$_3$)$_2$), 27.1 (C(CH$_3$)$_2$), 27.2 (C(CH$_3$)$_2$), 65.6 (CH$_2$, C-2), 75.7, 76.4, 76.5, 81.3 (4×CH, C-2, C-3, C-4), 110.9 (C(CH$_3$)$_2$), 114.7 (C(CH$_3$)$_2$), 173.3 (C=O).

Step 2: Synthesis of 2,3-O-isopropylidene-D-gulono-lactone

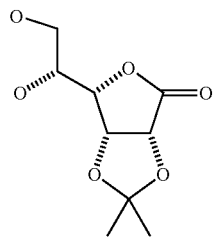

2,3;5,6-Di-O-isopropylidene-D-gulono-1,4-lactone (26 g, 0.1 mol) was dissolved in aquous acetic acid (200 ml, 80%) and the solution was stirred overnight at room temperature. T.l.c. (ethyl acetate) showed the consumption of starting material ($R_f$ 0.8) and the formation of one major product ($R_f$ 0.4). The reaction solvent was removed and the residue crystallized from ethyl acetate/hexane to give 2,3-O-isopropylidene-D-gulono-1,4-lactone (20.7 g, 95 mmol, 95%) as a white solid.

M.p. 139-141° C.; $[\alpha]_D^{22}$ +73.1 (c, 2.4 in acetone); $\delta_H$ (200 MHz, CDCl$_3$): 1.21, 1.22 (2×s, 6H, C(CH$_3$)$_2$), 3.46-3.57 (m, 2H), 3.64-3.73 (m, 1H), 4.48 (dd, 1H, J$_{3,4}$ 5 Hz, J$_{4,5}$ 3Hz, H-4), 4.75 (d, 1H, J$_{2,3}$ 5 Hz, H-2), 4.81 (dd, 1H, J$_{2,3}$ 5 Hz, J$_{3,4}$ 3 Hz, H-3); $\delta_C$ (50 MHz, CDCl$_3$): 26.0 (C(CH$_3$)$_2$), 26.1 (C(CH$_3$)$_2$), 62.7 (CH$_2$, C-6), 71.3 (CH, C-3), 76.7, 77.1 (2×CH, C-4, C-5), 81.8 (CH, C-2), 113.9 (C(CH$_3$)$_2$), 175.5 (C=O).

Step 3: Synthesis of 2,3-O-isopropylidene-L-lyxono-1,4-lactone

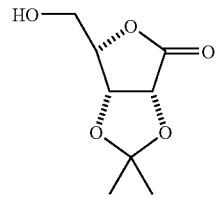

2,3-O-isopropylidene-D-gulonolactone (10.9 g, 50 mmol) was dissolved in dry THF (250 mL) under N$_2$. Periodic acid (12.8 g, 56 mmol, 1.12 eq) was added. After 5 min, the solution became cloudy and was vigorously stirred for another 15 min. The reaction mixture was purified by elution through a silica plug eluted with ethyl acetate. The solvent was removed under reduced pressure to afford a yellow oil which was dissolved in acetic acid (150 ml). Sodium cyanoborohydride (3.22 g, 51 mmol) was added and the solution stirred for 90 min. Saturated aqueous ammonium chloride solution (20 mL) was added to quench the reaction mixture and the solvent was removed under reduced pressure. The residue was dissolved in ethyl acetate (200 mL) and washed with saturated aqueous ammonium chloride solution (50 ml), water (50 mL) and brine (50 mL). The aqueous layer was re-extracted with ethyl acetate (3×50 mL). The organic fractions were combined, dried (magnesium sulphate), filtered and the solvent removed. Purification by flash chromatography (ethyl acetate) gave 2,3-O-isopropylidene-L-lyxono-1,4-lactone (7.93 g, 42 mmol, 84% yield) as a white crystalline solid.

M.p. 94-95° C.; $[\alpha]_D^{23}$ −90.8 (c, 1.08 in acetone); $\delta_H$ (500 MHz, CDCl$_3$): 1.41, 1.49 (6H, 2×s, C(CH$_3$)$_2$), 2.18 (1H, br, OH), 3.87 (1H, dd, J$_{4,5'}$ 5.3 Hz, J$_{5,5'}$ 12.3 Hz, H-5'), 4.15 (1H, dd, J$_{4,5}$ 6.4 Hz, J$_{5,5'}$ 12.3 Hz, H-5), 4.56 (1H, ddd, J$_{4,5'}$ 5.3 Hz, J$_{4,5}$ 6.6 Hz, J$_{3,4}$ 3.6 Hz, H-4), 4.82 (1H, d, J$_{2,3}$ 5.5 Hz, H-2), 4.85 (1H, dd, J$_{3,4}$ 3.6 Hz, J$_{2,3}$ 5.5 Hz, H-3); $\delta_C$ (50 MHz, CDCl$_3$): 26.2 (C(CH$_3$)$_2$), 27.1 (C(CH$_3$)$_2$), 61.3 (CH$_2$, C-5), 76.6, 76.7, 79.8 (3×CH, C-2, C-3, C-4), 114.9 (C(CH$_3$)$_2$), 174.3 (C=O).

Step 4: Synthesis of 5-azido-5-deoxy-2,3-O-isopropylidene-L-lyxono-1,4-lactone

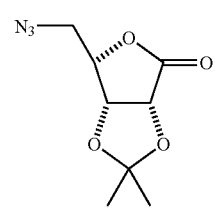

2,3-O-isopropylidene-L-lyxono-1,4-lactone (5.8 g, 30.9 mmol) was dissolved in anhydrous dichloromethane (140 mL) under N$_2$. The solution was cooled to −30° C. and dry pyridine (12 mL) was added. Trifluoromethanesulphonic anhydride (6.5 ml, 38.7 mmol) was then added dropwise to the solution which was stirred at −30° C. After 60 min, t.l.c. (ethyl acetate/hexane 1:1) showed a complete reaction. The solution was allowed to warm to 0° C. and dry DMF (250 ml)

and sodium azide (8.2 g, 126 mmol, 4 eq) were added. The suspension was stirred at room temperature for 4 Water (25 mL) was added to quench the reaction. The solvent was then removed under reduced pressure and co-evaporated with toluene. The residue was dissolved in dichloro methane (250 mL) and washed water (2×50 mL) and brine (50 mL). The aquous layer was re-extracted with dichloro methane (3×50 mL). The organic fractions were combined, dried (magnesium sulphate), filtered and the solvent removed. Purification by flash chromatography (hexane/ethyl acetate 1:1) afforded 5-azido-5-deoxy-2,3-O-isopropylidene-L-lyxono-1,4-lactone (5.8 g, 27.2 mmol, 88% yield) as white crystals. $[\alpha]_D^{23}$ −71.0 (c, 2.0 in CHCl$_3$); $\upsilon_{max}$ (film/cm$^{-1}$) 1784 (C=O), 2101 (N$_3$); $\delta_H$ (500 MHz, CDCl$_3$): 1.42, 1.50 (6H, 2×s, C(CH$_3$)$_2$), 3.66 (1H, dd, J$_{4,5'}$ 6.3 Hz, J$_{5,5'}$12.9 Hz, H-5'), 3.72 (1H, dd, J$_{4,5}$ 7.1 Hz, J$_{5,5'}$, 12.9 Hz, H-5), 4.62 (1H, ddd, J$_{4,5'}$, 6.3 Hz, J$_{4,5}$ 7.1 Hz, J$_{3,4}$ 3.5 Hz, H-4), 4.83 (1H, dd, J$_{3,4}$ 3.5 Hz, J$_{2,3}$ 5.4 Hz, H-3), 4.86 (1H, d, J$_{2,3}$ 5.4 Hz, H-2); $\delta_C$ (50 MHz, CDCl$_3$): 26.3 (C(CH$_3$)$_2$), 26.5 (C(CH$_3$)$_2$), 50.4 (CH$_2$, C-5), 76.1, 76.4, 77.6 (3×CH, C-2, C-3, C-4), 115.1 (C(CH$_3$)$_2$), 173.4 (s, C=O); m/z (CI, NH$_3$): 218 (100%), 186 (35%, MH$^+$-N$_2$); (Found: C, 45.26; H, 5.43; N, 19.24. C$_8$H$_{11}$O$_4$N$_3$ requires: C, 45.07; H, 5.20; N, 19.71%).

Step 5: Synthesis of 6-Azido-1,6-dideoxy-3,4-O-isopropylidene-L-lyxo-2,5-hexulose

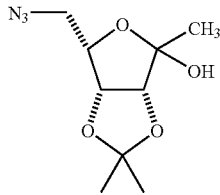

5-Azido-5-deoxy-2,3-O-isopropylidene-L-lyxono-1,4-lactone (4 g, 18.8 mmol) was dissolved in dry THF (70 mL) under N$_2$ in presence of molecular sieves (4Å). The solution was cooled to −78° C. Methyl lithium (18 ml, 25.2 mmol, 1.4 M solution in diethyl ether) was added and the solution stirred at −78° C. After two hours, t.l.c. (ethyl acetate/hexane 1:1) showed no starting material (Rf 0.62) and a new product (Rf 0.72). Saturated aqueous ammonium chloride solution (10 mL) was added and the solution was stirred for 30 min. The reaction mixture was then extracted with dichloromethane (4×50 mL). The organic extracts were combined, dried (magnesium sulphate), filtered off and the solvent removed under reduced pressure. The resulting yellow solid was purified by flash chromatography (ethyl acetate/hexane 1:2) to give 6-azido-1,6-dideoxy-3,4-O-isopropylidene-L-lyxo-2,5-hexulose (3.49 g, 91% yield) as a white solid.

M.p. 89-90° C.; $[\alpha]_D^{21}$ −12.5 (c, 1.01 in CHCl$_3$); $\upsilon_{max}$ (KBr)/cm$^{-1}$: 3436 (br, OH), 2101 (N$_3$); $\delta_H$ (500 MHz, CDCl$_3$): 1.33, 1.48 (6H, 2×s, C(CH$_3$)$_2$), 1.54 (3H, s, CH$_3$), 2.13 (1H, br, OH), 3.54 (2H, d, J$_{6',6}$ 6.4 Hz, H-6, H-6'), 4.23 (1H, app. dt, J$_{5,4}$ 3.9 Hz, J$_{5,6}$ 6.4 Hz, H-5), 4.48 (1H, d, J$_{3,4}$ 5.9 Hz, H-3), 4.78 (1H, dd, J$_{4,3}$ 5.9 Hz, J$_{4,5}$ 3.9 Hz, H-4); $\delta_C$ (50 MHz, CDCl$_3$): 22.9 (CH$_3$, C-1), 25.2, 26.5 (2×CH$_3$, C(CH$_3$)$_2$), 50.4 (CH$_2$, C-6), 77.9, 80.9, 85.8 (3×CH, C-3, C-4, C-5), 105.9 (C-2), 113.4 (C(CH$_3$)$_2$); m/z (APCI+): 216 (92%), 202 (MH$^+$-N$_2$, 38%), 184 (MH$^+$-H$_2$O-N$_2$, 100%); (Found: C, 47.38; H, 6.53; N, 18.03%; C$_9$H$_{15}$O$_4$N$_3$ requires C, 47.16; H, 6.60; N, 18.33%).

Step 6: Synthesis of 1,5,6-trideoxy-1,5-imino-3,4-O-isopropylidene-D-galactitol

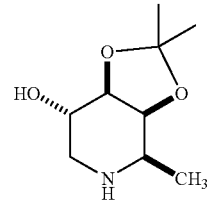

6-Azido-1,6-dideoxy-3,4-O-isopropylidene-L-lyxo-2,5-hexulose (1.0 g, 4.4 mmol) was dissolved in ethanol (25 mL). Palladium black (300 mg) was added. The solution was degased 3 times and air was replaced by H$_2$. The solution was stirred at room temperature under an atmosphere of H$_2$. After 24 hr, the solution was filtered through a celite plug eluted with ethanol. The solvent was removed under reduced pressure to give a yellow solid which was purified by flash chromatography (chloroform/methanol 4:1) to afford 1,5,6-trideoxy-1,5-imino-3,4-O-isopropylidene-D-galactitol as a white solid (700 mg, 3.7 mmol, 84% yield).

M.p. 164-166° C.; $[\alpha]_D^{22}$ +84.0 (c, 1.01 in CHCl$_3$); $\upsilon_{max}$ (cm$^{-1}$): 3434 (br, OH, NH); $\delta_H$ (500 MHz, CDCl$_3$): 1.27 (3H, d, J$_{5,6}$ 6.3 Hz, CH$_3$), 1.38, 1.55 (6H, 2×s, C(CH$_3$)$_2$), 1.95 (1H, br, OH), 2.48 (1H, dd, J$_{1a,2}$ 10.6 Hz, J$_{1e,1a}$ 13.0 Hz, H-1a), 3.08 (1H, dq, J$_{4,5}$ 2.6 Hz, J$_{5,6}$ 6.3 Hz, H-5), 3.12 (1H, dd, J$_{1e,2}$ 5.1 Hz, J$_{1a,1e}$ 13.0 Hz, H-1e), 3.67 (1H, ddd, J$_{1',2}$ 5.1 Hz J$_{1,2}$ 10.6 Hz, J$_{2,3}$ 7.1 Hz, H-2), 3.88 (1H, dd, J$_{2,3}$ 7.1 Hz, J$_{3,4}$ 5.3 Hz, H-3), 4.04 (1H, dd, J$_{4,5}$ 2.6 Hz, J$_{3,4}$ 5.3 Hz, H-4); $\delta_C$ (50 MHz, CDCl$_3$): 18.0 (CH$_3$, C-6), 26.7, 28.7 (2×CH$_3$, C(CH$_3$)$_2$), 48.7 (CH$_2$, C-1), 51.6 (CH, C-5), 71.1, 77.0, 80.5 (3×CH, C-2, C-3, C-4), 109.5 (C(CH$_3$)$_2$); m/z (APCI+): 188 (MH$^+$, 100%), 130 (19%); (Found: C, 57.26; H, 9.40; N, 7.24%. C$_9$H$_{17}$O$_3$N requires C, 57.73; H, 9.15; N, 7.48%)

Step 7: Synthesis of N-nonyl-1,5,6-trideoxy-1,5-imino-3, 4-O-isopropylidene D-galactitol

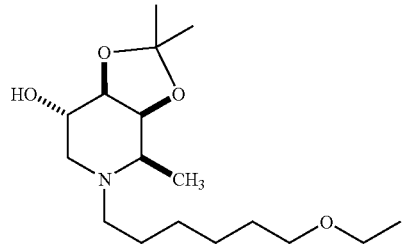

1,5,6-trideoxy-1,5-imino-3,4-O-isopropylidene-D-galactitol (804 mg, 4.3 mmol) was dissolved in ethanol (15 mL). Glacial acetic acid (0.1 mL) and 6-ethoxy-hexanol (1.83 g, 12.9 mmol, 2.2 ml, 3 eq) were added. After stirring the reaction mixture for 20 min at room temperature under N$_2$. Palladium black (300 mg) was added. The solution was degassed three times and nitrogen was replaced by H$_2$. The solution was stirred at room temperature under an atmosphere of H$_2$. After 16 h, the solution was filtered through a celite plug eluted with ethanol (50 mL) and ethyl acetate (40 mL). The solvent was removed under reduced pressure to give a yellow solid which was purified by flash chromatography (ethyl acetate) to afford N-nonyl-1,5,6-trideoxy-1,5- imino-3,4-O-isopropylidene-D-galactitol as a white solid (829 mg, 2.7 mmol, 63% yield).

M.p. 41-43° C. ; $\delta_H$ (200 MHz, CDCl$_3$): 0.99 (3H, t, J 7.3 Hz, CH$_3$), 1.22-1.51 (15H, 6×CH$_2$, CH$_3$, C-6), 1.35, 1.53 (6H, 2×s, C(CH$_3$)$_2$), 2.32 (1H, t, J 10.3 Hz, H-1a), 2.52-2.96 (m, 3H, H-5, N-CH$_2$), 3.82-3.94 (2H, m, H-1e, H-4); 4.12 (1H, m, H-2); $\delta_C$ (50 MHz, CDCl$_3$): 14.6 (CH$_3$), 16.0 (CH$_3$, C-6), 23.1, 24.4 (2×CH$_3$, C(CH$_3$)$_2$), 27.9, 29.7, 29.9, 32.3 (4×CH$_2$), 53.4 (CH$_2$, C-1), 54.1 (CH$_2$, N-CH$_2$), 55.1 (CH, C-5), 70.2, 78.1, 79.7 (3×CH, C-2, C-3, C-4), 109.6 (C(CH$_3$)$_2$);

Step 8: Synthesis of N-(7-oxa-nonyl)-1,5,6-trideoxy-1,5-imino-D-galactitol

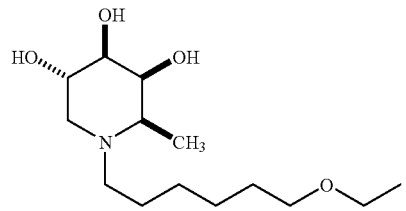

N-nonyl-1,5,6-trideoxy-1,5-imino-3,4-O-isopropylidene-D-galactitol (1.4 g, 4.5 mmol) was dissolved in 50% aqueous trifluoroacetic acid (10 mL) and the solution was stirred for two hours. The solvent was removed under reduced pressure and co-evaporated with toluene (2×5 mL). Purification by flash chromatography (CHCl$_3$/CH$_3$OH 3:1) afforded N-nonyl-1,5,6-trideoxy-1,5-imino-D-galactitol (1.18 g, 4.3 mmol, 96% yield);

M.p. 49-51° C.; $\upsilon_{max}$ (cm$^{-1}$): 3434 (br, OH), 2845 (N-CH$_2$), 1672 (N-CH$_2$), 1203, 1133; $\delta_H$ (200 MHz, d$^4$-MeOH): 0.99 (3H, t, J 7.3 Hz, CH$_3$), 1.22-1.51 (15H, 6×CH$_2$, CH$_3$, C-6), 2.88 (1H, t, J 10.6 Hz, H-1a), 3.16 (2H, m, N-CH$_2$), 3.31 (1H, m, H-5), 3.42 (1H, dd, J$_{1e,2}$ 5.0 Hz, J$_{1a,1e}$ 10.6 Hz, H-1e), 3.51 (1H, dd, J$_{4,5}$ 2.6 Hz, J$_{3,4}$ 5.3 Hz, H-4); 3.91 3.51 (1H, dd, J$_{4,5}$ 2.6 Hz, J$_{3,4}$ 5.3 Hz, H-4); 4.08 (1H, ddd, J$_{1',2}$ 5.1 Hz J$_{1,2}$ 10.6 Hz, J$_{2,3}$ 7.1 Hz, H-2), $\delta_C$ (50 MHz, CDCl$_3$): 13.4 (CH$_3$), 13.6 (CH$_3$, C-6), 22.1, 22.7, 26.7, 29.3, 29.5, 32.0 (6×CH$_2$), 52.9 (CH$_2$, N-CH$_2$), 54.2 CH$_2$, C-1), 60.9, 65.5, 71.9, 74.1 (4×CH, C-2, C-3, C-4, C-5); m/z (APCI$^+$): 274.2 (MH$^+$, 100%).

Preparation of N-7-oxa-nonyl-DGJ, N-7-oxa-nonyl-methylDGJ, N-7-oxa-nonyl-DMDP, and N-7-oxa-nonyl-2-aminobenzamide The parent amino or imino compound (DGJ, MeDGJ, DMDP, or 2-aminobenzamide (2ABC9) was reductively alkylated with 6-ethoxy-hexanal (1.2 mol equivalents) in the presence of one mole equivalent of sodium cyanoborohydride for three hours at room temperature in acidified methanol. Typical yields from this reaction were greater than 95% as determined by amperometric detection after high performance cation-exchange chromatography (Dionex). N-7-oxa-nonyl-compounds were purified from the reaction mixture by high performance liquid chromatography (HPLC) as follows. A sample was applied to a SCX cation-exchange column (7.5×50 mm) in 20% (v/v) acetonitrile and eluted with a linear gradient of 20% acetonitrile containing 500 mM ammonium formate, pH 4.4. The N-7-oxa-nonyl compound was recovered and applied to a C18 reverse-phase column (4.6×250 mm) equilibrated with 10% acetonitrile containing 0.1% trifluoroacetic acid (TFA). The compound was eluted from the column using a linear gradient of 80% acetonitrile containing 0.1% trifluoroacetic acid, lyophilized to dryness, and dissolved in methanol. Samples of purified compound were analyzed by matrix-assisted laser desorption ionization time-of-flight (MALDI-TOF) mass spectrometry using 2,5-dihydroxybenzoic acid as the matrix.

Compounds having different N-7-oxa-alkyl chain lengths are prepared by replacing oxanonyl-aldehyde with the desired chain length aldehyde. Tritiated compounds are prepared by employing tritiated sodium cyanoborohydride as the reducing agent in the reaction.

Characterization of Synthesized Compounds

N-(7-oxa-nonyl)-1,5,6-trideoxy-1,5-imino-D-galactitol (chloride salt)

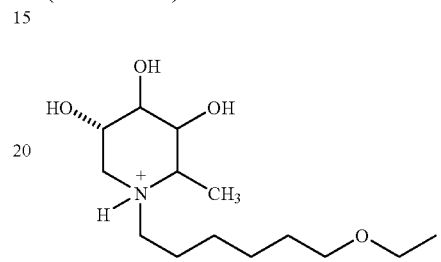

N-(7-oxa-nonyl)-1,5,6-trideoxy-1,5-imino-3,4-O-isopropylidene-D-galactitol (70 mg, 0.22 mmol) was dissolved in 50% aqueous trifluoroacetic acid (1 mL) and the solution was stirred for two hours. The solvent was removed under reduced pressure. Purification by flash chromatography (CHCl$_3$/CH$_3$OH 3:1) afforded N-(7-oxa-nonyl)-1,5,6-trideoxy-1,5-imino-D-galactitol (60 mg, 0.21 mmol, 96% yield). The compound was dissolved in water (1 mL) and aqueous hydrogen chloride solution (0.18 ml, 2M, 1 eq.) was added (pH 2). The reaction mixture was stirred for three hours, after this time t.l.c. (CHCl$_3$/MeOH 4:1) showed consumption of the starting material (r$_f$=0.19) and one baseline spot. The solvent was removed under reduced pressure and the remaining solid was freeze dried for 24 hr to give a yellow solid (65 mg, 0.23 mmol, 99%). The following data is for the product prior to treatment with HCl:

$\delta_H$ (200 MHz, d$^4$-MeOH): 1.15 (311, t, J 7.1, CH$_3$), 1.39 (3H, d, J 6.5, CH$_3$, C-6), 1.45-1.81 (10H, 5×CH$_2$), 2.92 (1H, t, J 10.6 Hz, H-1a), 3.02-3.18 (2H, m, H-1e, H-5); 3.22-3.62 (8H, m, N-CH$_2$, 2×O-CH$_2$, H-2, H-4), 4.04-4.12 (2H, m, H-3, H-4); $\delta_C$ (50 MHz, CDCl$_3$): 13.6 (CH$_3$), 14.5 (CH$_3$, C-6), 22.0, 25.8, 26.5, 29.5 (4×CH$_2$), 52.8 (CH$_2$, C-1), 54.2 (CH$_2$, N-CH$_2$), 61.0 (CH, C-5), 66.2, 70.4, (2×CH$_2$, CH$_2$-O-CH$_2$), 65.5, 71.9, 74.1 (3×CH, C-2, C-3, C-4); m/z (APCI$^+$): 276.2 (MH$^+$, 100%).

Toxicity of various chain length N-alkyl DNJ in MDBK cells are shown in Table 1.

TABLE 1

| N-alkyl Chain Length | % Viability at 10 μM | % Viability at 100 μM |
|---|---|---|
| C$_4$ | 74 | 77 |
| C$_5$ | 80 | 70 |
| C$_6$ | 73 | 71 |
| C$_8$ | 70 | 71 |
| C$_9$ | 56 | 41 |
| C$_{10}$ | 73 | 43 |
| C$_{12}$ | 86 | 1 |
| C$_{16}$ | 88 | 4 |
| C$_{18}$ | 84 | 2 |

The inhibitory activity ($IC_{50}$) and the cell cytotoxicity ($IC_{50}$) of various compounds, as well as their effect on α-glucosidase and ceramide glucosyl transferase, are shown in Table 2.

TABLE 2

| Compound | Inhibitor of α glucosidase | Inhibitor of glycolipid synthesis | Anti-viral effect on BVDV in MDBK cells | | Selectivity index ($CC_{50}/IC_{50}$) |
|---|---|---|---|---|---|
| | | | $IC_{50}$ | $CC_{50}$ | |
| DNJ | Yes | No | Yes 20 μM | ND | ND |
| N-butyl DNJ | Yes | Yes | Yes 60-120 μM | >>10 mM | >>100 |
| N-nonyl DNJ | Yes | Yes | Yes 2-3 μM | 250 μM | 83-125 |
| N-butyl DGJ | No | Yes | No | | |
| N-nonyl DGJ | No | Yes | Yes 5 μM | 250 μM | 50 |
| N-nonyl MeDGJ | No | No | Yes 2-3 μM | ND | ND |
| N-7-oxa-decyl DNJ | Yes | Yes | Yes 15-20 μM | 8 mM | 400-533 |
| N-7-oxa-nonyl MeDGJ | No | No | Yes 1.5 μM | 2.1 mM | 1400 |

Note the lack of cell cytotoxicity of the N-alkyl oxa-substituted compound and its superior selectivity index.

Other Materials and Methods

Cells and transfection: CHO, MDBK and Hep G2 cells were grown in RPMI 1640 (Gibco-BRL, Rockville, Md.) containing 10% fetal bovine serum (Gibco-BRL). Hep G2.2.15 cells were kindly provided by Dr. George Acs (Mt. Sinai Medical College (New York, N.Y.) and maintained in the same manner as Hep G2 cells but with the addition of 200 μg/ml of G418 (Gibco-BRL). DNA transfection of Hep G2 cells were performed as previously described (Bruss & Ganem, *Proc. Natl. Acad. Sci. USA* 88:1059-1063, 1991). N-butyl deoxynojiricmycin (NB-DNJ) was provided by Monsanto/Searle (St. Louis, Mo.). N-nonyl deoxygalactojirimycin (N-nonyl-DGJ) and N-nonyl deoxynojiricmycin (N-nonyl-DNJ) were provided by Synergy Pharmaceuticals (Somerset, N.J.).

Plaque Reduction and Yield Assays: MDBK cells were grown in six-well plates in the presence or absence of inhibitor, infected with cp BVDV (moi=0.005; 500 pfu per well) for one hour at 37° C. The inoculum was then replaced with growth medium alone or with growth media and the antiviral agent and incubated for two or three days in the presence or absence of inhibitor (plaque reduction assay). After counting the plaques by eye under the microscope, the supernatant containing secreted infectious virus was removed from the wells and used to infect a fresh monolayer of MDBK cells in six-well plates. After three days, the resulting plaques were counted under the microscope (yield assay).

Figure 5:
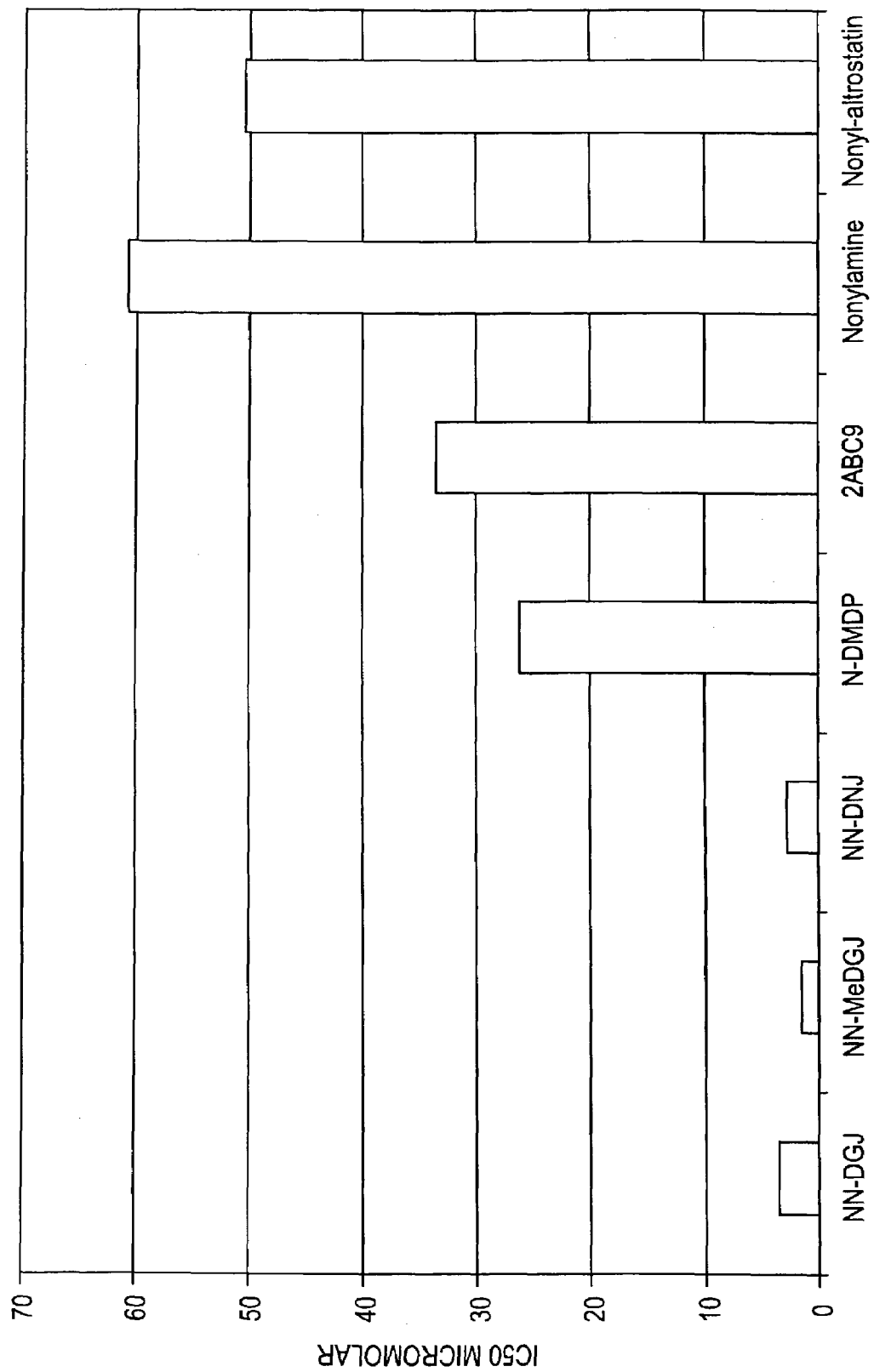
Figure 6:
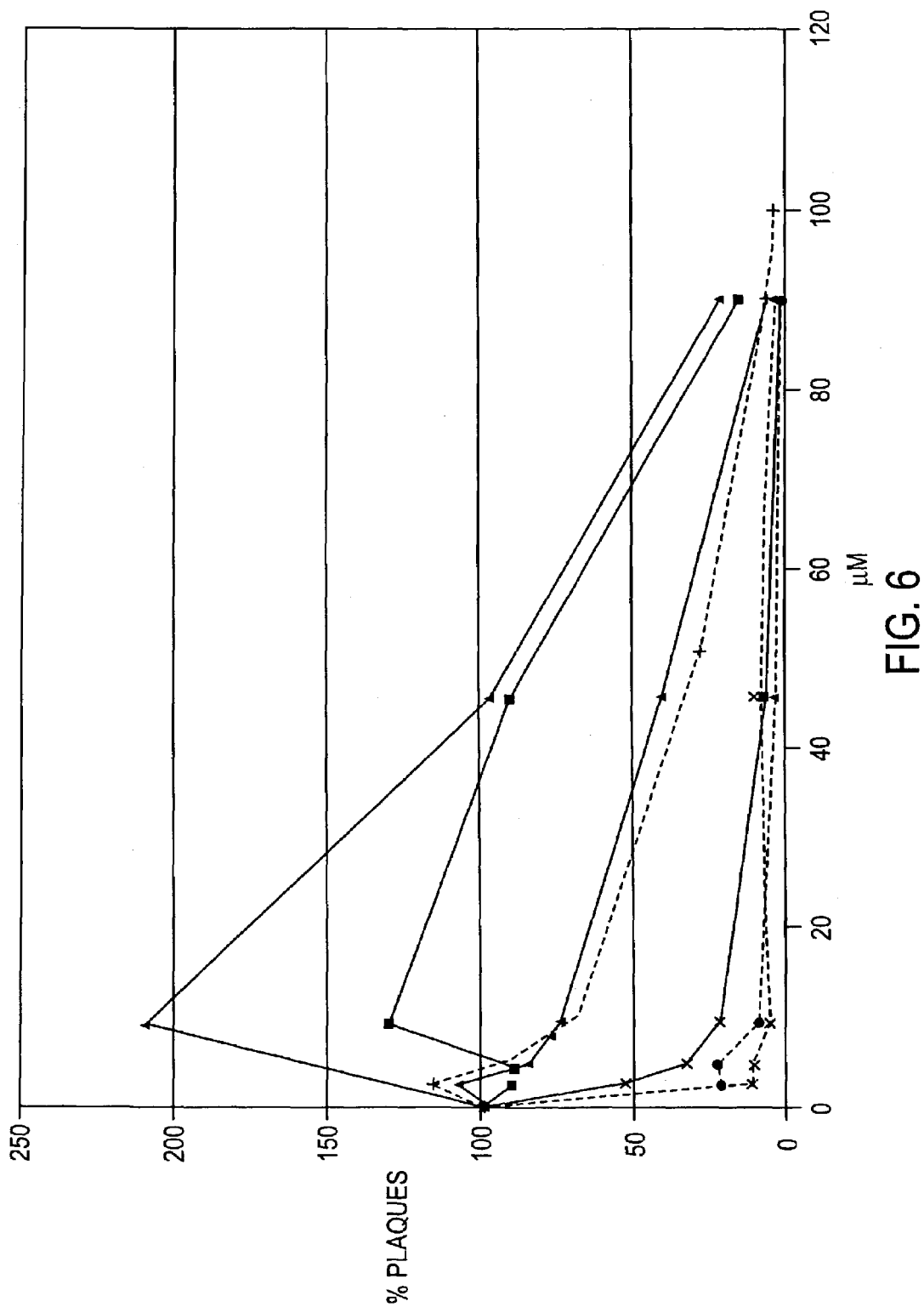
FIG. 6 depicts the percent of BVDV plaques produced by an infected cell culture in the presence of various concentrations of N-nonyl compounds: 2ABC9 (♦), nonylamine (■), N-nonyl-altrostatin (Δ), N-nonyl-DGJ (×), N-nonyl-MeDGJ (✱), N-nonyl-DNJ (●), or N-nonyl-DMDP (+).
Figure 7:
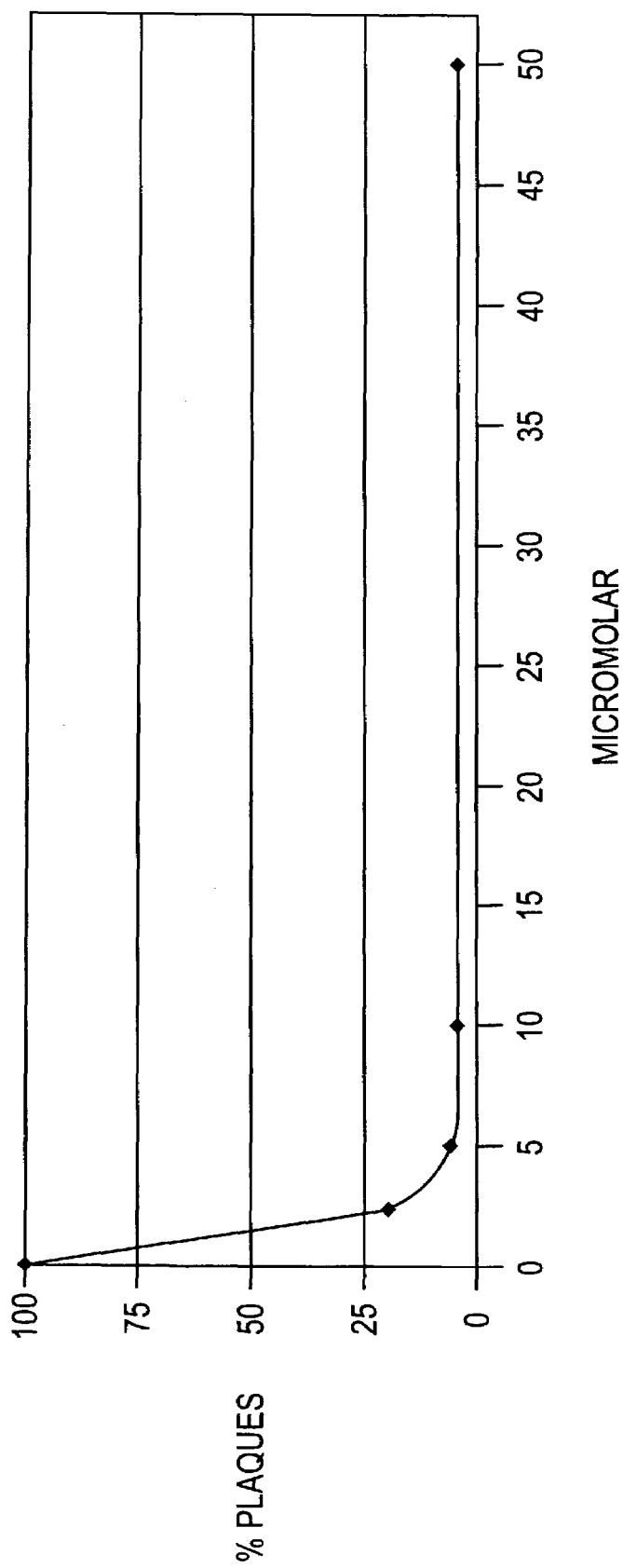
FIG. 7 depicts the percent of BVDV plaques produced by an infected cell culture in the presence of various concentrations of N-7-oxa-nonyl MeDGJ.

FIG. 5 is a bar graph showing average $IC_{50}$ values for N-nonyl-DGJ, N-nonyl-MeDGJ, N-nonyl-DNJ, N-DMDP, N-nonyl-2-aminobenzamide (ABC9), nonylamine, and N-nonyl-altrostatin. The percent of BVDV plaques produced by an infected cell culture in the presence of different concentrations of 2ABC9 (♦), nonylamine (■), N-nonyl-altrostatin (Δ), N-nonyl-DGJ (×), N-nonyl-MeDGJ (✳), N-nonyl-DNJ (●), and N-nonyl-DMDP (+) are shown in FIG. 6. $IC_{50}$ values for N-nonyl-MeDGJ was less than about 2.5 μM as shown in FIG. 7.

Secreted DNA analysis: Secreted DNA analysis was performed by the method of Wei et al. (*J. Virol.* 70:6455-6458, 1996). Hep G2.1.15 cells were seeded at 85-90% confluency in T-75 flasks and three days later the indicated drug added at the specified concentrations: 3TC (1 μM unless noted); N-butyl-DNJ (4.52 mM); N-nonyl DNJ (either 7 μM, 70 μM or 100 μM as noted); N-nonyl-DGJ (either 7 μM, 70 μM or 100 μM as noted). Media containing drug was changed every two days and on the 7th day the media taken and the virus concentrated by pelleting through 20% sucrose for 16 hours (SW 41 rotor, 36,000 RPM). Virus was resuspended in 400 μL of 10 mM TRIS (pH 7.9), 10 mM EDTA (pH 8.0), and 10 mM $MgCl_2$. Samples were split into two 200 μL aliquots and labeled as +Dnase and −Dnase. To both tubes, 15 μl of proteinase K was added to a final concentration of 750 μg/ml for one hour at 37° C. After one hour, 10 pl Dnase was added to the tube labeled +Dnase (final concentration is 50 units/ml) and incubated at 37° C. for one hour. SDS was added to a final concentration of 1% and additional proteinase K added to a final concentration of 500 μg/ml and the reaction allowed to proceed at 37° C. for 3-4 hours. DNA was than purified by phenol/chloroform extraction. DNA was separated on 1% agarose gel and probed with $^{32}P$ labeled probes as described (Mehta et al., *Proc. Natl. Acad. Sci. USA* 94:1822-1827, 1997).

Intracellular DNA analysis: Hep G2.2.15 cells were either left untreated or treated with the compounds listed above for seven days and the total DNA extracted as described (Mehta et al., ibid). DNA (20 μg) was digested with HindIII, resolved through a 1.2% agarose gel and transferred to nylon membranes. Membranes were then hybridized with a $^{32}P$ labeled probe containing the total HBV genome and developed as described (Lu et al., *Proc. Natl. Acad. Sci. USA* 94:2380-2385, 1997). The relaxed circular (rc), linear (lin), and closed circular (CCC) DNA were confirmed by enzymatic digestion.

Endogenous polymerase assay: Media containing HBV from Hep G2.2.15 cells was pelleted through 20% sucrose (SW 28 Rotor, 24,000 RPM) for 16 hours and the pellet re-suspended in 50 μl of a mixture containing 50 mM Tris (pH 7.5), 75 mM $NH_4Cl$, 1 mM EDTA, 25 mM $MgCl_2$, 0.1% β-mercaptoethanol, 0.5% NP-40, 0.4 mM each of dATP, dGTP, dTTP and 10 μl of $P^{32}$ labeled dCTP. Drug was added to a final concentration of 3TC (7 μM), NB-DNJ (5 mM), NN-DNJ (100 μM) and NN-DGJ (100μM) and the samples placed at 37° C. overnight and the next day proteinase K was added to a final concentration of 500 μg/ml and incubated at 37° C. for one hour. DNA was purified by a phenol/chloroform extraction and ethanol precipitation.

Secretion of Infectious BVDV in the Presence of Long Chain N-Alkyl Compounds

Figure 2:
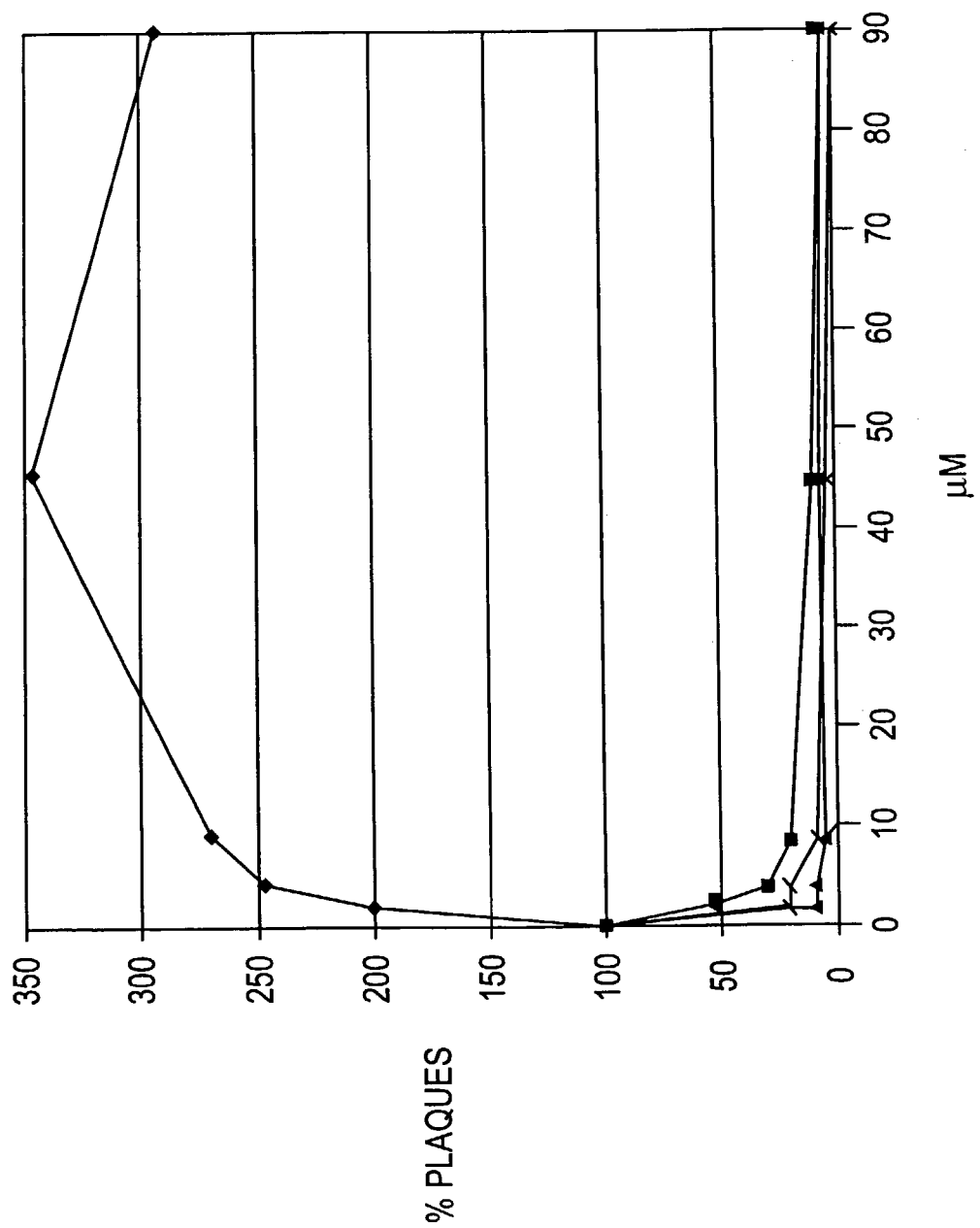
FIG. 2 depicts the percent of BVDV plaques produced by an infected cell culture in the presence of various concentrations of compounds: N-butyl DGJ (♦), N-nonyl DGJ (■), N-nonyl MeDGJ (▲), or N-nonyl DNJ(×).
Figure 3:
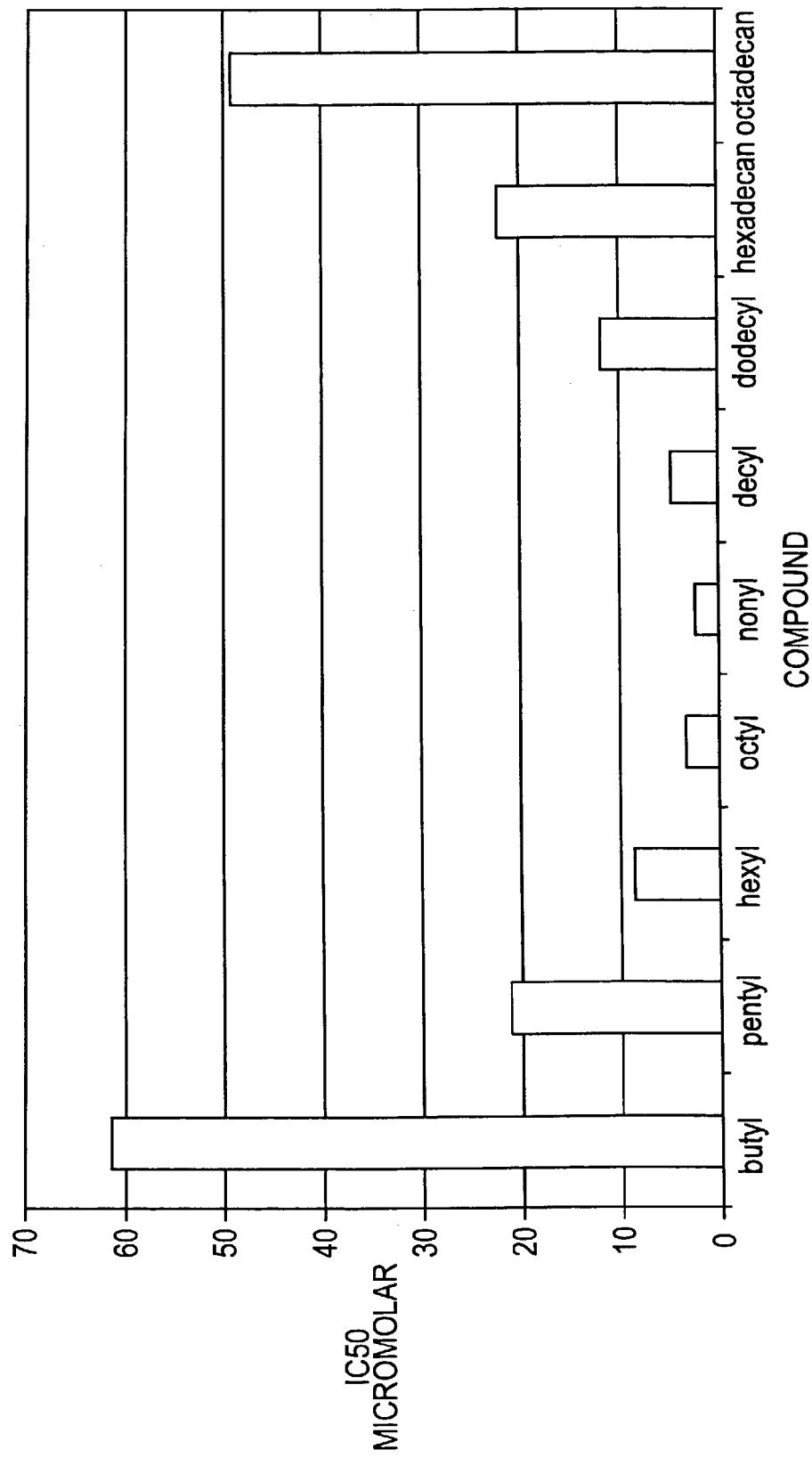
FIGS. 3 depicts the $IC_{50}$ of various alkyl lengths of N-alkylated compounds and FIG. 5 depicts the $IC_{50}$ of N-nonyl compounds.
Figure 4:
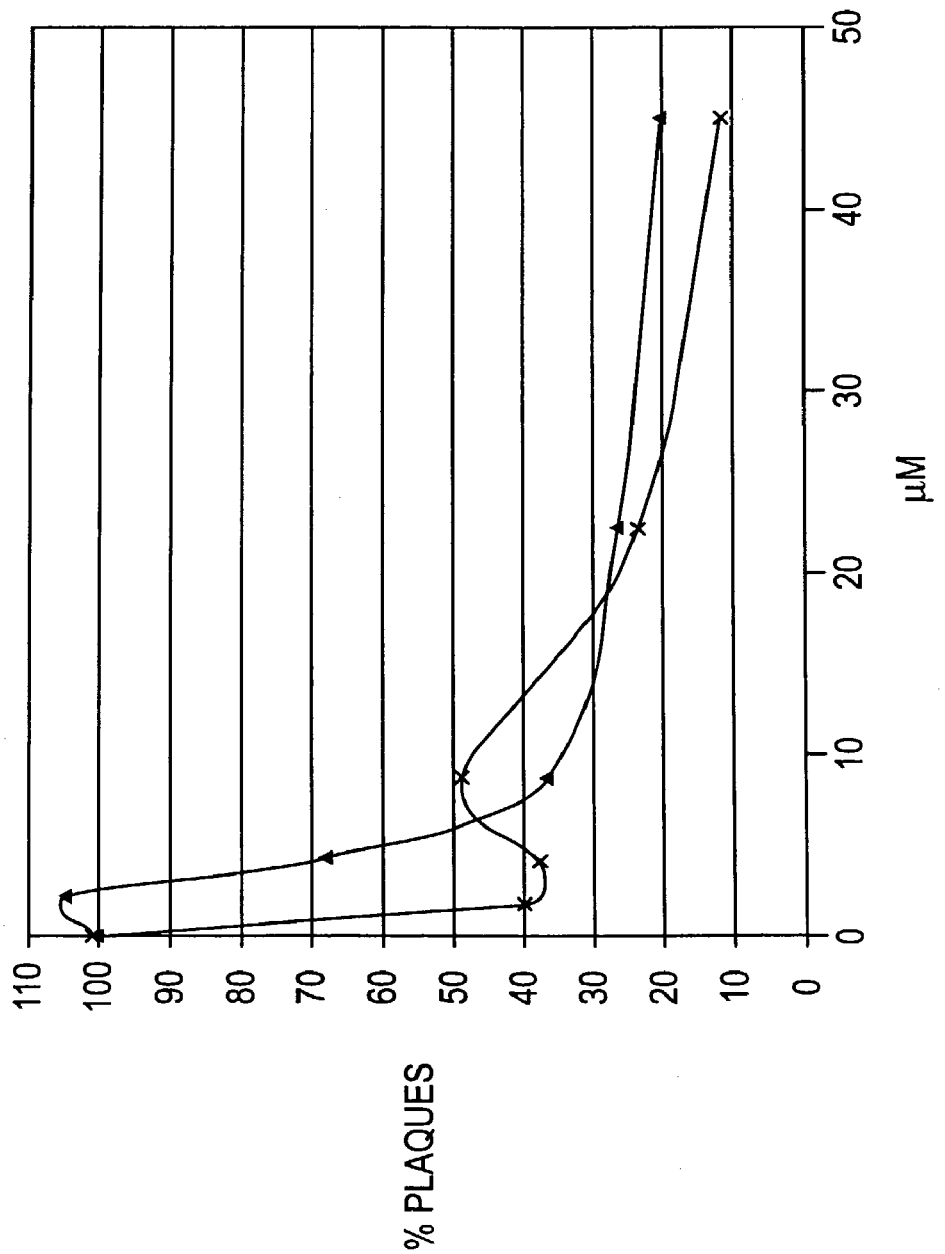
FIG. 4 depicts the percent of BVDV plaques produced by an infected cell culture in the presence of various concentrations of N-nonyl DGJ (▲) or N-decyl DGJ (×).

MDBK cells were grown to semi-confluence in individual wells of 24-well plates. The cells were then infected by BVDV by incubating the cells for one hour at 37° C. in the presence of approximately 500 PFU of the NADL strain of BVDV suspended in growth medium. The inoculum was then replaced with growth medium alone or growth medium containing a particular concentration of a long chain N-alkyl compound. After three days, the supernatants were removed and used to infect fresh MDBK monolayers in six-well plates. After three days, the cell monolayers were observed microscopically before and after staining with 0.2% (w/v) crystal violet in ethanol for plaque counting, and 0.2% neutral red for viability and the presence and number of virus-induced plaques was determined. The results were expressed as percentages of the number of plaques resulting from infection with the inhibitor-free plaque assay supernatant (=100%). The results of these experiments are presented in the graphs depicted in FIG. 2, FIG. 3, and FIG. 4. FIG. 2 is a graph depicting the variation in $IC_{50}$ for N-alkylated DNJ compounds having the following chain lengths: butyl, pentyl, hexyl, octyl, nonyl, decyl, dodecyl, hexadecyl, and octadecyl.

Inhibitory constants for various chain length N-alkyl DNJ derivatives for ceramide glucosyl transferase (CerGlcT) and α-glucosidase are summarized in Table 3.

TABLE 3

| N-alkyl Chain Length | CerGlcT ($IC_{50}$, μM) | α-Glucosidase ($IC_{50}$, μM) |
|---|---|---|
| $C_4$ | 34.4 | 0.57 |
| $C_5$ | 26.8 | |
| $C_6$ | 23.8 | |
| $C_8$ | 16.8 | |
| $C_9$ | 7.4 | |
| $C_{10}$ | 3.1 | 0.48 |
| $C_{12}$ | 5.2 | |
| $C_{16}$ | 3.4 | |
| $C_{18}$ | 4.1 | |

Uptake of Radioactively Labeled Inhibitors by Different Cell Types

Figure 8:
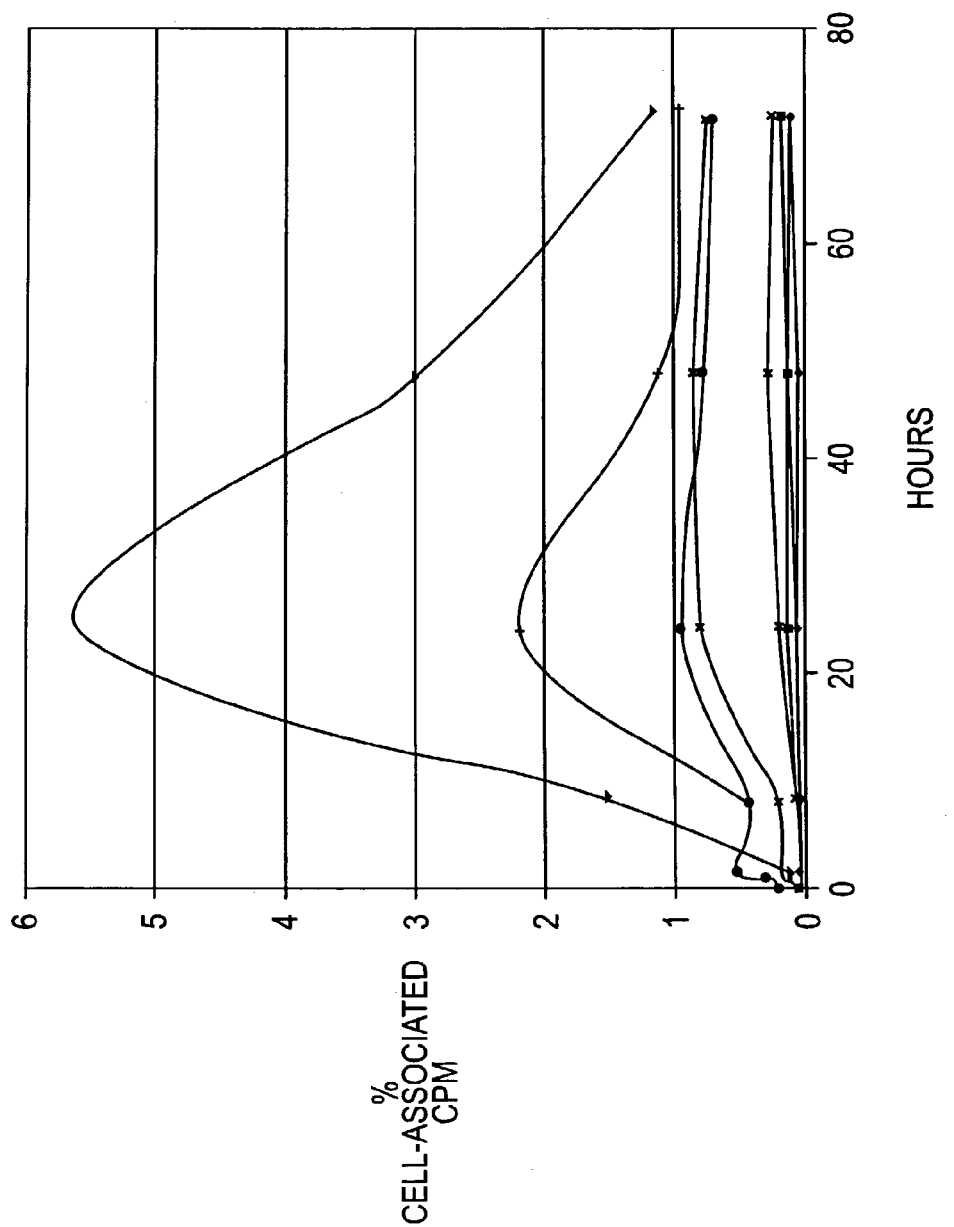
FIG. 8 depicts the increasing uptake of $^3$H-labeled inhibitors in HepG2 cells in the following order: N-butyl-DNJ (♦), N-hexyl-DNJ (■), N-octyl-DNJ (▲), N-nonyl-DNJ (×), N-decyl-DNJ (✱), N-dodecyl-DNJ (●), N-hexadecan-DNJ (+), or N-octadecan-DNJ (—).

MDBK and HepG2 cells were grown to confluency in 12-well plates and incubated in the presence of tritiated long chain N-alkylated compounds (100,000 cpm/well) for the times indicated in FIG. 7. The supernatant was removed and kept. The cells were washed with PBS (2×500 μL), fixed with 500 μL of ice-cold 10% perchloric acid/2% phosphotungstic acid, washed twice with 500 μL of icecold ethanol, air dried, and lysed overnight at room temperature with 500 μL of 0.5 M NaOH. The percentage of radioactive counts in the supernatant, PBS wash and lysed cells was determined by liquid scintillation counting. The results are shown graphically in FIG. 8.

Secretion of HBV in the Presence of Lamivudine, NN-DNJ and NN-DGJ

Hep G 2.2.15 cells are a stably transfected line of HepG2 hepatoblastama cells that contain a dimer of the HBV genome and produce and secrete infectious HBV. This is a cell line that has been used as a standard in the pre-clinical evaluation of HBV antiviral agents, as enveloped HBV can be detected in the culture medium by antigen capture methods. The ability of NN-DGJ to inhibit enveloped HBV secretion from 2.2.15 cells was compared with lamivudine (3TC) and NN-DNJ, using the antigen capture method, described previously. Briefly, 2.2.15 cells were grown to confluence and then incubated with the indicated concentrations of compound. At 6 and 9 days after incubation in the presence of compound, the amount of enveloped HBV in the culture medium was determined by PCR amplification of viral DNA from samples obtained by immunoprecipitation with HbsAg specific antibody. The results after nine days of incubation are shown in Table 4. Medium collected after nine days of incubation contained easily detectable amounts of HBV. As expected, 3TC (lamivudine) was effective in reducing the amount of enveloped HBV in the culture medium, when compared with the untreated controls. NN-DGJ was at least as effective as NN-DNJ in reducing the HBV secretion. The IC50 values for NN-DNJ and NN-DGJ Were about 1 and 0.5 μM, respectively, in this assay. MTT assays of these cultures revealed that no measurable toxicity was observed for the concentrations used and time of exposure. These results showed that NN-DGJ is effective in preventing the secretion of HBV from Hep G2.2.15 cells at micromolar concentrations.

TABLE 4

Secretion of Hepatitis B virus (HBV) from Hep G2.2.15 cells in the absence and presence of antiviral compounds

| COMPOUND[1] | IC 50[2] | TOX 50[3] |
|---|---|---|
| 3TC | 5 uM | >100 uM |
| NN-DNJ | 0.4-4 uM | >100 uM |
| NN-DGJ | 1.5-5 uM | >200 uM |

[1] 2.2.15 cells were grown to confluence in 96 well trays and the amount of HBV in the culture medium determined by an antigen capture/PCR based assay after 6 and 9 days of incubation the absence or presence of three concentrations of either 3TC (lamivudine), NN-DNJ or NN-DGJ. Pairs of wells were used for each concentration point.

[2] IC 50: The concentration of compound that prevented the secretion of 50% of the amount of HBV detected in the medium from wells containing untreated cultures. IC 90s were achieved for each of the compounds used.

[3] TOX 50: The concentration of compound that reduced the amount of MTT activity to 50% of that of the untreated controls, as determined on the cultures at the conclusion of the experiment (10 days). Note that because Tox 50s were not reached with even the highest concentrations of compounds used, values are given as ">" (more than).

Effect of N-nonyl-DGJ on Secretion of HBV as Measured by Southern Blot Hybridization HepG2.2.15 cells were grown for seven days in the absence or presence of NB-DNJ (1000 μg/ml), NN-DNJ (20 μg/ml) or NN-DGJ (20 μg/ml), respectively. After seven days, virus was isolated from these cell cultures, concentrated, and purified. Secreted HBV DNA was detected by Southern blot hybridization. HBV viral DNA from untreated cells was readily detected. The secretion of HBV DNA from treated HepG2.2.15 was also detected. N-butyl-DNJ and N-nonyl-DNJ caused a small decrease of about 3-fold and 1.5-fold secreted virus DNA, respectively; whereas N-nonyl-DGJ showed a considerably greater reduction of about 14-fold.

Intracellular Levels of HBV DNA in HepG2.2.15 Cells Grown in the Presence of 3TC, and Various Iminosugars An infected cell contains several forms of HBV DNA which represent different stages in the HBV life cycle. For example, covalently closed circular DNA (CCC DNA) is the nuclear form of the DNA and is thought to be the viral template (Heermann & Gerlich, 1992). In contrast, the relaxed circular DNA (re DNA) and linear forms (lin) are associated with the viral particle and their presence is an indicator of encapsidation of the viral pre-genomic RNA and the subsequent reverse transcription into progeny DNA (Ganem, Curr. Top. Microbiol. Immunol. 168:61-83, 1991). The accumulation of intracellular HBV DNA from HepG2.2.15 cells left untreated or treated with 3TC (1 μg/ml), NB-DNJ (1000 μg/m1), NN-DNJ (2 μg/m1 or 20 μg/ml), or NN-DGJ (2 μg/ml or 20 μg/ml) was determined as described above. The amount of virus associated with the cells was detected seven days later by Southern blot analysis. The locations of the HBV relaxed circular DNA (rcDNA), covalently close circular (CCC) DNA, and single stranded (SS) DNA was identified by relative mobility.

HBV relaxed circular DNA (rc DNA) is easily observed, as are the smaller replicative intermediates. Treatment with 3TC leads to a complete disappearance of intracellular HBV DNA. This is consistent with 3TC acting as a polymerase inhibitor and preventing DNA production (Doong et al., *Proc. Natl. Acad. Sci. USA* 88:8495-8499, 1991). In contrast, treatment with N-butyl-DNJ causes a dramatic increase in the replicative forms of HBV DNA (Mehta et al., *Proc. Natl. Acad. Sci. USA* 94:1822-1827, 1997). This finding is consistent with the action of this drug in preventing viral envelopment and budding but having no direct effect on DNA synthesis. Surprisingly, N-nonyl-DNJ did not cause a large increase in intracellular HBV DNA but rather a reduction. This reduction was even more pronounced with N-nonyl-DGJ, leading to an almost complete disappearance of intracellular HBV DNA (greater than 25 fold). This result clearly differentiates the action of N-nonyl-DNJ and N-nonyl-DGJ from N-butyl-DNJ.

Effect of Lamivudine and Iminosugars on HepG2.2.15 Polymerase Activity

HBV DNA replication involves the conversion of a pregenomic RNA (pgRNA) into DNA by the action of the HBV polymerase. Current nucleoside analogue drugs (e.g., 3TC) for treating HBV target this reaction, preventing the formation and secretion of HBV viral DNA. Because the iminosugar N-nonyl-DGJ prevents the formation of HBV rc DNA, it was important to determine whether N-nonyl-DGJ was acting by inhibiting the elongation step of the polymerase. HBV virions from normal and drug treated Hep G2.2.15 cells were purified and the endogenous polymerase activity was measured. HBV virions were purified from the culture medium of untreated cells by ultracentrifugation and the polymerase activity (in the presence of the indicated compounds) tested by the method of Ganem et al. (1998). Briefly, partially purified viral particles were incubated overnight with the indicated concentrations of compound and 10 μCi of $^{32}$P-dCTP. Viral DNA was purified by phenol extraction and ethanol precipitation and resolved on a 1.2% agarose gel. The gel was dried and viral DNA bands detected using a Phospholmager.

The activity of polymerase from untreated virons was measured by incorporation of radioactive nucleotides into rc DNA. In contrast, treatment with 3TC (20 μM) inhibited polymerase activity. This is consistent with 3TC acting as a polymerase inhibitor. N-butyl-DNJ (4.52 mM) showed no effect on polymerase activity, consistent with its mechanism as an α-glucosidase inhibitor. Both N-nonyl-DNJ (69 μM) and N-nonyl-DGJ (69 μM) also had no effect on polymerase activity, although both these drugs were shown above to cause a significant decrease in intercellular HBV DNA levels. These data suggest that these alkyl chain derivatives must inhibit the formation or stability of the HBV DNA by an alternative method than inhibition of polymerase activity.

All cited publications, books, patents, and patent applications are incorporated by reference in their entirety where they are cited including the priority documents U.S. patent application Ser. No. 60/148,101 filed Aug. 10, 1999 and U.S. patent application Ser. No. 60/198,621 filed Apr. 20, 2000.

From the foregoing, it would be apparent to persons skilled in the art that the invention can be embodied in other specific forms without departing from its spirit or essential characteristics. For example, all combinations of the embodiments described above are considered part of the invention with the proviso that the prior art is excluded. The described embodiments should be considered only as illustrative, not restrictive, because the scope of the invention will be indicated by the appended claims rather than by the foregoing description. All modifications which come within the meaning and range of the lawful equivalency of the claims are to be embraced within their scope. In that sense, no particular order of process steps is intended unless explicitly recited.

The invention claimed is:

1. A compound having the formula

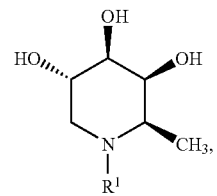

wherein $R^1$ an oxa-substituted derivative of a $C_8$-$C_{16}$ alkyl or a pharmaceutically acceptable salt or solvate of said compound.

2. The compound of claim 1, wherein the compound is N-nonyl-1,5,6-trideoxy-1,5-imino-D-galactitol (N-nonyl MeDGJ), or a physiologically acceptable salt thereof.

3. The compound of claim 1, wherein the compound is N-(7-oxa-nonyl)-1,5,6-trideoxy-1,5-imino-D-galactitol (N-7-oxa-nonyl MeDGJ), or a physiologically acceptable salt thereof.

4. The compound of claim 1, wherein $R^1$ is a $C_8$-$C_{16}$ alkyl.

* * * * *